(12) United States Patent
Stearns et al.

(10) Patent No.: US 11,083,581 B2
(45) Date of Patent: Aug. 10, 2021

(54) EXPANDABLE HEART VALVE COAPTATION DEVICE

(71) Applicant: Edwards Lifesciences Corporation, Irvine, CA (US)

(72) Inventors: Grant Matthew Stearns, Costa Mesa, CA (US); Alexander J. Siegel, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 218 days.

(21) Appl. No.: 16/208,264

(22) Filed: Dec. 3, 2018

(65) Prior Publication Data

US 2019/0167429 A1 Jun. 6, 2019

Related U.S. Application Data

(60) Provisional application No. 62/594,277, filed on Dec. 4, 2017.

(51) Int. Cl.
*A61F 2/24* (2006.01)

(52) U.S. Cl.
CPC .......... *A61F 2/2463* (2013.01); *A61F 2/2442* (2013.01); *A61F 2/2454* (2013.01); *A61F 2/2466* (2013.01); *A61F 2/246* (2013.01); *A61F 2210/0057* (2013.01); *A61F 2210/0061* (2013.01); *A61F 2220/0075* (2013.01); *A61F 2220/0091* (2013.01); *A61F 2230/001* (2013.01); *A61F 2250/0003* (2013.01)

(58) Field of Classification Search
CPC .............. A61F 2/2463; A61F 2/2442; A61F 2230/001; A61F 2210/0061; A61F 2250/0003
See application file for complete search history.

(56) References Cited

U.S. PATENT DOCUMENTS

| | | | |
|---|---|---|---|
| 7,628,797 B2 | 12/2009 | Tieu et al. | |
| 8,382,829 B1 | 2/2013 | Call et al. | |
| 8,758,431 B2 | 6/2014 | Orlov et al. | |
| 9,510,948 B2 | 12/2016 | Padala | |
| 2004/0092858 A1* | 5/2004 | Wilson .................. | A61F 2/2427 604/9 |

(Continued)

FOREIGN PATENT DOCUMENTS

| | | |
|---|---|---|
| WO | 2013036742 A1 | 3/2013 |
| WO | 2017151566 A1 | 9/2017 |

*Primary Examiner* — Anh T Dang

(57) ABSTRACT

In one embodiment, an expandable positioning device for improving the coaptation of heart valve leaflets is provided. The expandable positioning device can include one or more expandable members. A first expandable member extends below a leaflet in order to reposition the leaflet to improve coaptation with another leaflet. A second expandable member extends above a leaflet in order to secure the expandable delivery device at the implantation site. The expandable positioning device can include a neck that is inserted through the leaflet on which the device is implanted. The expandable positioning device can include a coupling member to releasably couple the device to a delivery device. One or more sealing members can be included in the expandable positioning device to maintain a desired level of expansion of the one or more expandable members.

20 Claims, 11 Drawing Sheets

(56) References Cited

U.S. PATENT DOCUMENTS

| | | |
|---|---|---|
| 2007/0250087 A1* | 10/2007 | Makower .......... A61B 17/07292 |
| | | 606/157 |
| 2008/0039935 A1 | 2/2008 | Buch et al. |
| 2008/0281356 A1 | 11/2008 | Chau et al. |
| 2009/0043381 A1 | 2/2009 | Macoviak et al. |
| 2012/0022629 A1* | 1/2012 | Perera .................... A61F 2/2418 |
| | | 623/1.11 |
| 2012/0310330 A1* | 12/2012 | Buchbinder ....... A61M 25/1011 |
| | | 623/2.11 |
| 2013/0116794 A1* | 5/2013 | Shohat ................ A61F 2/30756 |
| | | 623/19.11 |
| 2013/0289604 A1* | 10/2013 | Brister .................. A61M 29/02 |
| | | 606/192 |
| 2014/0031864 A1 | 1/2014 | Jafari et al. |
| 2014/0243968 A1* | 8/2014 | Padala .................... A61F 2/246 |
| | | 623/2.36 |
| 2015/0230919 A1 | 8/2015 | Chau et al. |
| 2016/0089234 A1 | 3/2016 | Gifford, III |
| 2016/0158497 A1 | 6/2016 | Tran et al. |
| 2016/0278920 A1 | 9/2016 | Braido et al. |
| 2017/0049571 A1 | 2/2017 | Gifford, III |
| 2018/0071093 A1 | 3/2018 | Navia et al. |
| 2018/0325661 A1 | 11/2018 | Delgado et al. |

\* cited by examiner

EXPANDABLE HEART VALVE COAPTATION DEVICE

CROSS-REFERENCE TO RELATED APPLICATION

This application claims the benefit of U.S. Provisional Patent Application No. 62/594,277, filed Dec. 4, 2017, which is incorporated by reference herein.

FIELD

The present disclosure generally relates to heart valve repair, and more particularly to devices and related methods for improving coaptation between heart valve leaflets.

BACKGROUND

The native heart valves (i.e., the aortic, pulmonary, tricuspid, and mitral valves) serve critical functions in assuring the unidirectional flow of an adequate supply of blood through the cardiovascular system. These heart valves can be rendered less effective by congenital malformations, inflammatory processes, infectious conditions, or disease. Such damage to the valves can result in serious cardiovascular compromise or death.

For many years the definitive treatment for such disorders was the surgical repair or replacement of the valve during open heart surgery. However, such surgeries are highly invasive, and are prone to many complications. Therefore, elderly and frail patients with defective heart valves often went untreated. More recently, transcatheter techniques have been developed for introducing and implanting prosthetic devices in a manner that is much less invasive than open heart surgery. Such transcatheter techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle.

The mitral valve has a very different anatomy than other native heart valves. The mitral valve includes an annulus portion, which is an annular portion of the native valve tissue surrounding the mitral valve orifice, and a pair of cusps or leaflets extending downward from the annulus into the left ventricle. The mitral valve annulus can form a "D" shaped, oval, or otherwise out-of-round cross-sectional shape having major and minor axes. The anterior leaflet can be larger than the posterior leaflet, forming a generally "C" shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords, called chordae tendineae, tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. There are many different causes of mitral regurgitation. One particular cause is excessive slack in at least one of the native leaflets. This excessive slack prevents the native leaflets from effectively closing during the systolic phase of heart contraction, thus allowing mitral regurgitation. In another case, the heart may have structural defects such that the leaflets are too far apart to provide sufficient coaptation of the leaflets to prevent flow to the left atrium during systole. In another case, the ventricle may be enlarged, pulling the leaflet coaptation edge away from the base too far below the annular plane towards the apex of the heart, preventing proper coaptation of the leaflets.

Various devices and methods for treating mitral regurgitation have been developed, including implanting a prosthetic valve within the native mitral valve, surgically removing a portion of the native heart valve leaflets to reduce excessive slack, or clipping or otherwise coupling the leaflets to improve coaptation. These devices and methods can, however, be highly invasive, require lengthy or complex procedures, or require an extensive recovery period.

Thus, there is a continuing need for improved devices and methods for repairing native heart valve leaflets.

SUMMARY

Described herein are embodiments of a device that is primarily intended to be used to reposition the leaflets of the mitral, aortic, tricuspid, or pulmonary heart valves, as well as methods for implanting such device. The device can be used to improve coaptation of heart valve leaflets.

In one representative embodiment, an expandable positioning device can include one or more expandable members. A first expandable member can be positioned against an inferior leaflet surface and expanded to reposition the leaflet closer to an opposing native leaflet of the heart valve. A second expandable member can be positioned against a superior leaflet surface when implanted in an atrium of the heart and expanded to secure the positioning device on the native leaflet. The expandable positioning device is also secured at the implantation site by the first and second expandable portions having a diameter larger than an opening in the leaflet through which the device was inserted. In various examples, the first and second expandable members can be of unitary construction/part of a common structure (e.g., a single balloon) or can be multiple structures (e.g., multiple balloons) coupled together.

In some embodiments, the expandable positioning device can include one or more cords that can be used to constrain a diameter of the device, such as a diameter of the first expandable portion proximate the inferior leaflet surface.

In some embodiments, the expandable positioning device can include features to facilitate delivery and implantation. For example, a distal portion of the expandable positioning device can include a nose cone that facilitates atraumatic tracking through a patient's vasculature. A proximal portion of the expandable positioning device can include a coupling member that can be used to couple the expandable positioning device to a delivery device during delivery and deployment.

The expandable positioning device can include one or more sealing members to maintain a desired degree of fluid pressure within the one or more expandable members. For example, a portion of the expandable positioning device coupled to a delivery device can include a sealing member, such that the sealing members seals when an expansion tube (e.g., used to deliver an expansion fluid or to otherwise cause expansion of at least one of the expandable members) is retracted into the delivery device. When an expandable positioning member includes multiple expandable members, a sealing member can be disposed between expandable members to maintain fluid pressure, including different fluid pressures, within the expandable members.

The expandable portions, including when provided by different expandable members, can be of similar or different construction, including size, shape, and material. Similarly, when fluids are used to expand (such as to inflate) expandable members, the fluids can be the same or different, including phase of matter, density, weight, and composition.

A portion of the expandable positioning device intermediate the first and second expandable portions can have a reduced diameter, and be configured to be placed within a leaflet, and to maintain an axial separation between the first and second expandable portions. The reduced diameter portion can have a flexible axial length, such that the length can accommodate varying degrees of expansion of the first and second expandable portions.

In some embodiments, the expandable positioning device can include an enclosure that contains a mass of an expandable material. The expandable material can be a swellable material, such as a hydrogel. The expandable material can be selectively expandable, and in some cases contractable, including by exposing the expandable material to a fluid, to a fluid having a suitable temperature, to a fluid having a suitable pH, to electrical stimuli, or to radiation.

The enclosure can have additional features, such as a variable-width opening. The size of the opening can be controlled, in some cases, using a cord that is secured to the enclosure and encircles the opening. The cord can be placed under a desired degree of tension to provide a desired opening size. When the opening size is desired to be fixed, the cord can be secured with the appropriate degree of tension using a locking member, such as a suture clip.

The enclosure can be permeable, such as being made from a mesh material, which can facilitate contacting the mass of expandable material with a physiological fluid, or to allow fluids introduced into the enclosure to pass out of the enclosure.

In a further aspect, the present disclosure provides a method for improving coaptation of heart valve leaflets. The method can include delivering an expandable positioning device to a heart valve, such as the mitral valve, using a delivery device. The expandable positioning device can be inserted through a leaflet to be repositioned. A first expandable portion of the expandable positioning device can be expanded to provide a desired degree of repositioning to the leaflet, such as to provide a desired improvement to coaptation with another leaflet. When a desired repositioning has been achieved, a second expandable portion of the expandable positioning device can be expanded to secure the device to the leaflet. The delivery device can then be removed from the patient.

In some embodiments, the method can include expanding (such as inflating) the first expandable portion using a tube extending therein. The tube can be withdrawn, such as through a sealing member, into the second expandable portion. The second expandable portion can be expanded, and the tube withdrawn from the expandable positioning device. In a particular implementation, removing the tube from the expandable positioning device can release a coupling member that couples a delivery device to the expandable positioning device.

In some embodiments, the method includes constraining a diameter of the expandable positioning device, such as by tensioning a cord extending about a diameter of the expandable positioning device. The cord can be secured, such as using a locking device, to provide a desired level of tension to the cord, thus maintaining the cord at a desired diameter.

In some embodiments, an expandable positioning device can be removed after implantation. Removing the expandable positioning device can include contracting (such as deflating) the first and second expandable members, removing the expandable positioning device from the leaflet, and removing the expandable positioning device from the heart.

In some embodiments, the level of expansion (e.g., the size of an expandable member) of an expandable positioning device can be adjusted after implantation. An expansion tube can be inserted through a sealing member of the expandable positioning device. The tube can be placed in an expandable portion whose level of expansion or size is desired to be adjusted. In some implementations, fluid can be removed from, or added to, the expandable portion to achieve a desired degree of expansion. When the expandable portions have been adjusted to a desired size, the expansion tube can be removed from the expandable positioning device.

In further embodiments, the method can include adjusting the size of an opening of an expandable member of the expandable positioning device. Adjusting the opening size can include tensioning a cord coupled to the expandable member, where pulling the cord causes the opening size to be reduced. A locking member can be placed in contact with the cord to maintain the cord at a desired tension.

In another aspect, the present disclosure provides an assembly that includes an elongate delivery catheter having at least one lumen and an above-described expandable positioning device.

The foregoing and other objects, features, and advantages of the invention will become more apparent from the following detailed description, which proceeds with reference to the accompanying figures.

DETAILED DESCRIPTION

Described herein are embodiments of positioning devices, such as expandable positioning devices, that are primarily intended to be used to improve coaptation of the leaflets of the mitral, aortic, tricuspid, or pulmonary heart valves, as well as methods for delivering the same. The expandable positioning devices include one or more expandable portions on the atrial and ventricular sides of one or more leaflets. In some cases, an expandable positioning device includes a single expandable structure (e.g., a balloon or sack) that may have atrial and ventricular portions, which may be concurrently expandable, separately expandable, expandable to differing degrees, or combinations thereof. In further cases, an expandable positioning device can include a plurality of expandable structures (e.g., a plurality of balloons or sacks), which can be coupled to one another, and can be concurrently expandable, separately expandable, expandable to differing degrees, or combinations thereof. In a particular example, an expandable positioning device having multiple expandable members has an atrial expandable member and a ventricular expandable member.

Disclosed expandable positioning devices can include an expandable ventricular portion configured to push and/or reposition a heart valve leaflet such that the heart valve leaflet has improved coaptation with one or more other heart valve leaflets. For example, the posterior mitral valve leaflet can be pushed superiorly and anteriorly by a ventricular portion of the implant such that it has improved coaptation with the anterior mitral valve leaflet. An expandable atrial portion can expand against a superior surface of the heart valve leaflet to help secure the expandable positioning device at a desired position.

Disclosed expandable positioning devices can be introduced into the heart in any suitable manner. In a particular example, an expandable positioning device can access a heart valve using a minimally invasive technique, such as a transcatheter technique. For example, a delivery device can access the mitral valve using a transcatheter technique to deliver an expandable positioning device to the left atrium or left ventricle. In a particular example, an expandable positioning device can be introduced into the left atrium of a subject using a catheter, inserted through the posterior mitral valve leaflet, and expanded to a desired degree in vivo, including to provide desired degrees of repositioning (using a ventricular portion) and securing (using an atrial portion).

Figure 1:
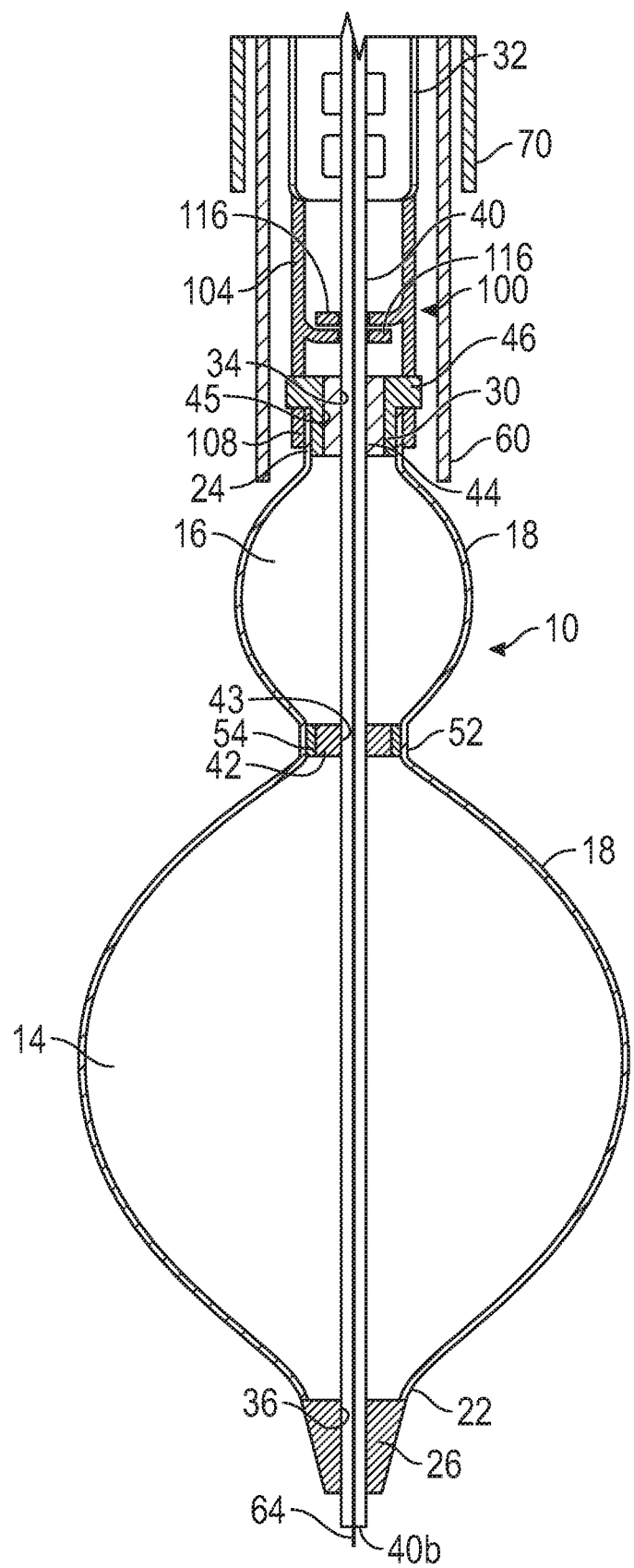
FIG. 1 is a cross-sectional view of an example expandable positioning device and a delivery device useable therewith.

Referring first to FIG. 1, there is shown a representative embodiment of an expandable positioning device 10 for improving coaptation of native or artificial heart valve leaflets. The expandable positioning device 10 can include a first expandable member 14 and a second expandable member 16. As shown in FIG. 1, in some implementations, the first expandable member 14 and the second expandable member 16 can be part of a unitary expandable body or structure 18, such as a balloon. In other implementations, the first expandable member 14 and the second expandable member 16 may comprise separate expandable bodies or structures (e.g., separate balloons), and may be appropriately secured to one another, such as using coupling member that can be inserted through a leaflet and to which the expandable members can be secured (e.g., by mechanical means or use of an adhesive or other type of bonding mechanism).

Whether the expandable members are different portions of same expandable structure or separate expandable structures, in certain embodiments the expandable members can be in fluid communication with each other, whereas in other embodiments, the expandable members can be fluidly separated or sealed off from each other. When an expandable positioning device 10 includes multiple separate bodies, the combined bodies can be considered as the body 18 for the purposes of the proceeding discussion.

Figure 8:
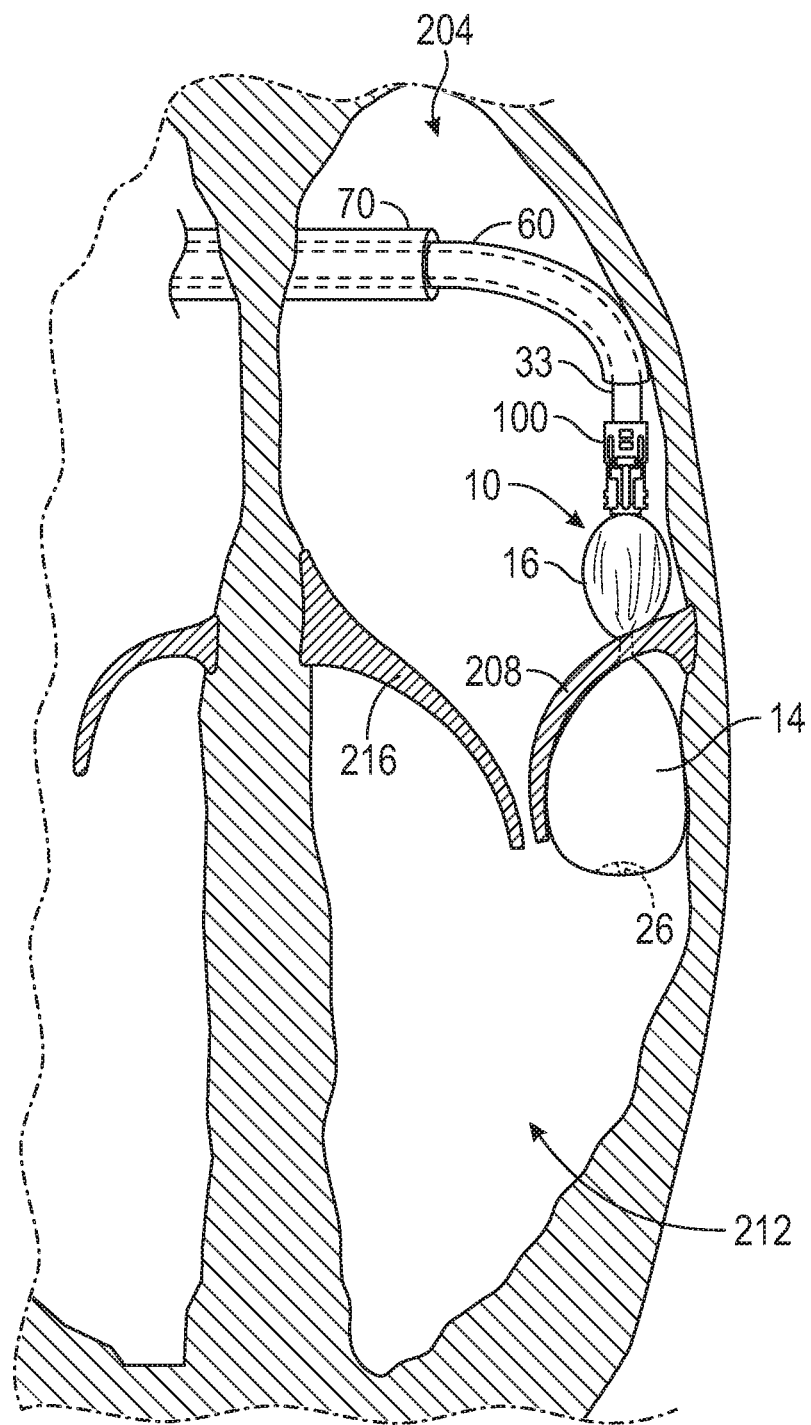

In particular embodiments, the first expandable member 14 is configured to be implanted within a ventricle of the heart and, when expanded, the expandable member can occupy space between the heart wall and the leaflet such that the leaflet is repositioned relative to the heart valve and the opposing native leaflet. FIG. 8, for example, shows the application of the expandable positioning device 10 to reposition the posterior mitral valve leaflet 208 relative to the anterior leaflet 216 to improve coaptation between the native leaflets 208, 216. As shown, the first expandable member 14, when expanded, occupies space between the wall of the left ventricle 212 and the posterior leaflet 208 so as to lift the posterior leaflet superiorly and toward the anterior leaflet. The second expandable member 16 is configured to expand against the opposite side of the posterior leaflet 208 from the first expandable member 14 to help secure the positioned device 10 in place. For example, in the procedure shown in FIG. 8, the second expandable member 16 is expanded against the superior surface of the posterior leaflet 208.

The expandable members 14, 16 can be constructed from any suitable material. Typically, the materials are compliant, stretchable materials that can expand as increasing amounts of an inflation medium are placed inside a hollow interior portion of the expandable members 14, 16. Thus, in some embodiments, the first and second expandable members 14, 16 can be first and second inflatable members, which can be separate portions of a single balloon or separate balloons that are coupled to each other. Suitable materials for forming the expandable members 14, 16 include polymers such as nylon, polyesters, polypropylenes, polytetrafluoroethylene, and expanded polytetrafluoroethylene.

In alternative embodiments, one or both of the first and second expandable members 14, 16 can contain an expandable mass that increases in size to expand the expandable members once the positioning device is implanted (as further described in detail below with respect to positioning device 300). That is, the expandable members 14, 16 can define an enclosure for an expandable fluid, an expandable material or mass, or a combination thereof. In a specific implementation, one or both of the expandable members 14, 16 are pre-filled with an expandable hydrogel, which can be in the form of hydrogel beads.

The body 18 (e.g., exterior surface) of the expandable members 14, 16 can be covered with another material or coating, such as to improve biocompatibility. In a specific example, the body 18 is coated with a fibrous material that encourages tissue ingrowth, such as electrospun polyethylene terephthalate fabric. In some embodiments, one or both of the first and second expandable members 14, 16 can be permeable to a selected fluid (e.g., blood), such as to permit contact between the selected fluid and an expandable mass (e.g., a hydrogel) contained inside the expandable member wherein such contact causes the mass to expand.

The body 18 can include a distal, insertion end 22 and a proximal, coupling end 24. The insertion end 22 can be configured to facilitate delivery to an implantation site in a subject. For example, a nose cone 26 can extend distally from the insertion end 22 of the body 18. The nose cone 26 can have a tapered outer surface for atraumatic tracking through a patient's vasculature.

The expandable positioning device 10 can include a proximal collar 30 affixed to the coupling end 24 of the body 18. The proximal collar 30 can facilitate releasably coupling of the expandable positioning device 10 to a shaft 33 (best shown in FIG. 2) of an implant delivery catheter 32. The proximal collar 30 can include can include a central opening 34 that is axially aligned with a bore 36 of the nose cone 26. The central opening 34 of the proximal collar 30 can be configured to slidably receive a shaft 40, which may be used to deliver an expansion fluid to expand the first expandable member 14 and the second expandable member 16 during an implantation procedure, as further described below. The proximal end of the shaft 40 can be fluidly connected to a source of an inflation medium. The shaft 40 can comprise, for example, a metal hypotube, an extruded shaft having one or more polymeric layers, or a combination thereof.

In some embodiments, the proximal collar 30, or another portion of the expandable positioning device 10 can include a sealing member 44, such as a hemostatic sealing member, configured to seal the central opening 34 when the shaft 40 is withdrawn from the central opening. In a specific example, the sealing member 44 can include flexible flaps that can pivot from a sealed configuration to an open configuration to allow the shaft 40 to extend through the central opening 34. When the shaft 40 is removed, the flaps can be configured to return to the sealed configuration from the open configuration. In another embodiment, the hemostatic sealing member 44 can be formed from an elastomeric (e.g., rubber) or other self-sealing material. When formed of an elastomeric material, a central bore 45 (best shown in FIG. 1) of the sealing member 44 can expand to accommodate passage of the shaft 40. When the shaft 40 is removed from the sealing member 44, the central bore 45 can close under the resiliency of the material.

After the expandable positioning device 10 is delivered to the target location (e.g., with the first expandable member 14 within a ventricle and the second expandable member 16 within an atrium on the same side of the heart), the shaft 40 can be retracted from the nose cone 26 until the distal end 40b of the shaft 40 is positioned within the first expandable member 14. A pressurized inflation medium (e.g., a liquid or gas) from the source can flow through a lumen of the shaft 40, outwardly from an opening at the distal end 40b and into the first expandable member 14. The user can control the amount of the inflation medium delivered to the first expandable member 14 until the first expandable member has been inflated to a desired degree. The shaft 40 can then be further retracted proximally until the distal end 40b is located within the second expandable member 16 to permit inflation of the second expandable member 16. When the second expandable member 16 has been inflated to a desired degree, the shaft 40 can be withdrawn from the expandable positioning device 10.

In alternative embodiments, the shaft 40 can include one or more side openings spaced along the length of the shaft to permit inflation of the first and/or second expandable members 14, 16 without retracting the shaft 40. For example, the shaft 40 can be formed with first and second lumens that separately deliver an inflation medium to the first and second expandable members 14, 16, respectively. The first lumen can extend through the shaft 40 from its proximal end to a first side opening formed in the shaft at a location within the first expandable member 14. The second lumen can extend through the shaft 40 from its proximal end to a side opening formed in the shaft at a location within the second expandable member 16. In this manner, the inflation medium can be delivered to the first and second expandable members through separate fluid pathways concurrently or consecutively. Instead of separate lumens, the inflation medium can be delivered to the first and second expandable members 14, 16 via separate conduits or tubes extending through the shaft 40 or apart from the shaft 40.

Other embodiments of an expandable positioning device 10 may be constructed in a manner such that a sealing member 44 is not used. For example, after filling the first and second expandable members 14, 16 with an inflation medium, a sealing material, such as an epoxy material, is placed within the central opening 34, or otherwise at an opening to the interior of the expandable positioning device 10 to seal the inflation medium within the expandable members. In some cases, the sealing material can be allowed to solidify, or set, or cure, prior to removing the delivery apparatus from the patient's body. Or, the expandable positioning device 10 can include a tube or conduit that allows an inflation medium to be introduced into the expandable members 14, 16. After the expandable members 14, 16 have been inflated to a desired degree, the tube of the expandable positioning device 10 can be crimped or pinched to prevent leakage of the inflation medium from the expandable members.

In one embodiment, for example, the shaft 40 is not removed from the expandable positioning device 10 after expansion of the expandable members 14, 16 and instead is crimped or pinched (e.g., with a suture clip or similar device) at a location proximal to the collar 30. The shaft 40 in this embodiment can be sized to form a seal against the inner surface of the collar 30 if a separate sealing member 44 is not used. The portion of the shaft 40 proximal to the location of the crimp or pinch can be severed and removed from the patient's body.

In another embodiment, the shaft 40 can terminate at a location proximal to the collar 30 and can be connectable to another shaft or conduit that extends to the proximal end of the delivery device. The shaft or conduit delivers an inflation medium to the shaft 40, and after inflating the positioning device 10, the shaft or conduit is de-coupled from the shaft 40. The shaft 40 can be provided with a seal that seals the inflation medium within the expandable positioning device 10.

Other portions of the expandable positioning device 10 (such as a neck 52 or a lumen 36 of the nosecone 26) can include a sealing member, which can be analogous to the sealing member 44, or otherwise be sealed as described above. For example, the inner lumen 36 of the nose cone 26 can include a seal that engages, or is sealed, after the shaft 40 is withdrawn from the nose cone in order to expand the expandable members 14, 16, as further described below. As shown in FIG. 1, the neck portion 52 can include a sealing member 42, which can be generally similar to the sealing member 44, and can include a bore 43 through which the shaft 40 extends during delivery and expansion of the first expandable member 14.

Figure 2:
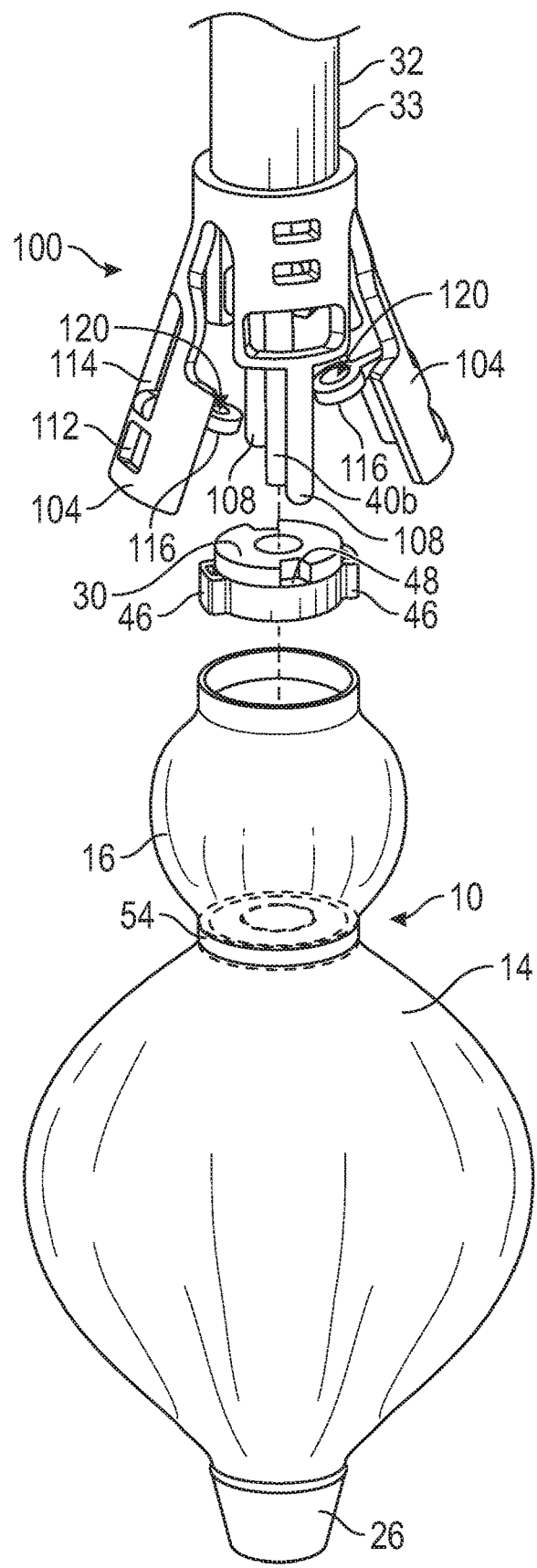
FIG. 2 is a perspective, partially-exploded view of the expandable positioning device and delivery device of FIG. 1.

As best shown in FIG. 2, the proximal collar 30 can also include a plurality of bosses or projections 46 and a plurality of guide openings 48. The projections 46 can extend radially outwardly and can be circumferentially offset (e.g., by 90 degrees) relative to the guide openings 48. The guide openings 48 can be disposed radially outwardly from the central opening 34. The projections 46 and the guide openings 48 of the proximal collar 30 can be configured to releasably engage a coupler 100 of the implant delivery catheter 32.

With continued reference to FIGS. 1 and 2, the first and second expandable members 14, 16 can be joined by a neck portion 52 of the body 18. In some cases, the neck portion 52 is integral to one or both of the expandable members 14, 16. In other cases, the neck portion 52 is separate from the expandable members 14, 16 and coupled to both of the expandable member 14, 16. The neck portion 52 can be made from a compliant material, such that the neck can axially lengthen or contract as the first and/or second expandable members 14, 16 are expanded or contracted. A neck portion 52 with an adjustable axial length can be beneficial, as it can facilitate different levels of expansion for the expandable members 14, 16, and to account for different leaflet tissue thickness, either at different possible implantation sites within a patient or to accommodate anatomical differences between patients.

In some implementations, the neck portion 52 can include an annular device, such as a rigid ring 54, or one or more tubular segments, that can help maintain a reduced diameter between the expandable members 14, 16, maintain an axial distance between the expandable members, or a combination thereof. As shown, the ring 54 can be mounted on the inside of the body 18, such as using an adhesive or welding to secure the ring 54 to the inner surface of the body 18. In other embodiments, the ring 54 can be mounted on the outside of the body 18. The ring 54 can be made of a material that is relatively stiffer or more rigid than the body 18 to prevent expansion of the body at the neck portion 52 beyond the diameter of the ring 54. The ring 54 can be made of any various metals or polymers. In some embodiments, the sealing member 42 (which can, in at least some cases, be analogous to the sealing member 44) can be disposed within the ring 54. The sealing member 42 can include a central bore 43 that allows passage of the shaft 40 and closes upon removal of the shaft to establish a seal within the neck portion 52 that fluidly separates the expandable members 14, 16 from each other.

The interior or exterior surfaces of the body 18 can include additional features. For example, a portion of the body 18, such as the neck portion 52, can house or support a radiopaque (fluoroscopic) or echogenic marker, which can be used to help locate and position the expandable positioning device 10 during implantation. In at least some cases, the marker can be, or can be incorporated into, or located on, the rigid ring 54. When an expandable member 14, 16 is asymmetrical, the marker can be used to confirm that the expandable member is positioned in a desired configuration.

Figure 9:
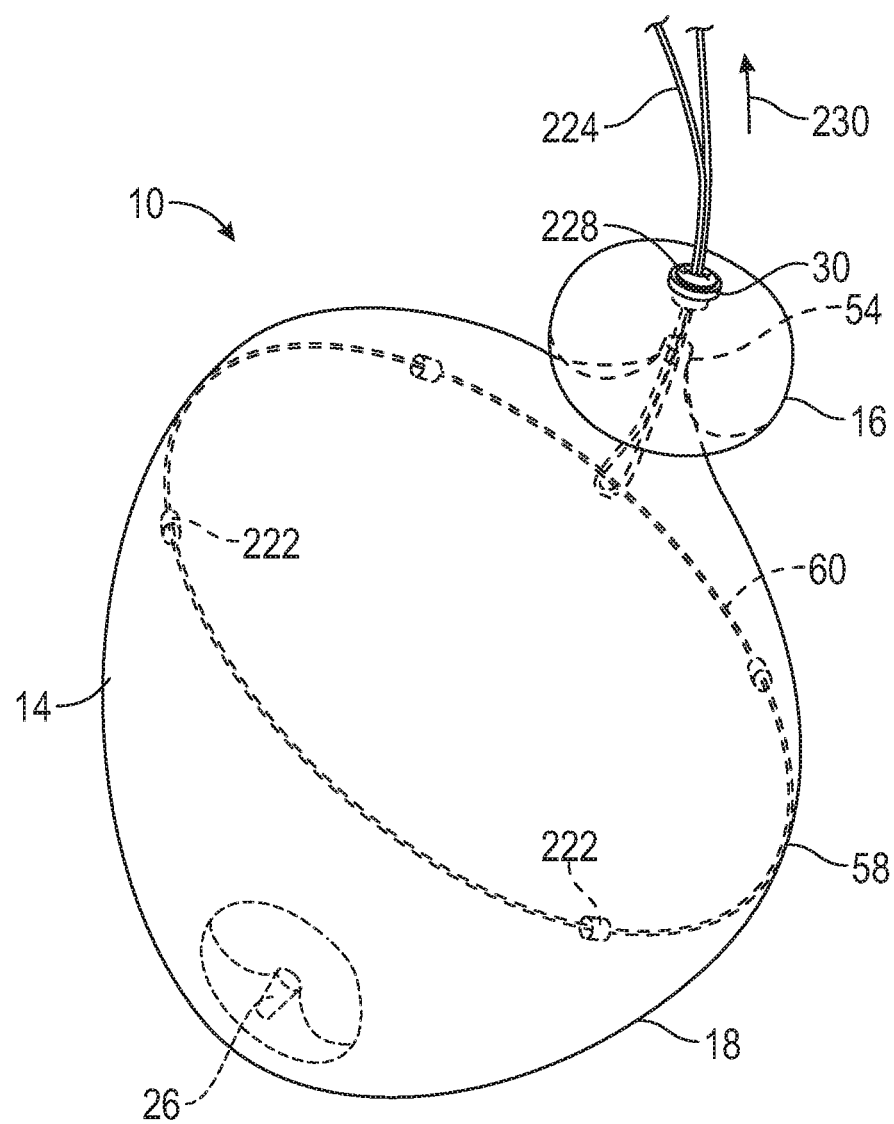
FIG. 9 is a perspective view of the expandable positioning device of FIGS. 1 and 2, in a fully expanded state, such as after implantation and expansion as shown in FIGS. 7 and 8, with a cord useable to constrain a diameter of the expandable positioning device.

With reference to FIG. 9, the body 18 can include a cord 60, which can be used to cinch an intermediate portion 58 of the body (a portion of the first expandable member 14, as shown) to a desired diameter. Depending on the position of the cord 60, the cord can be used to control the diameter of the neck portion 52 inserted through leaflet tissue, or a portion of an expandable member 14, 16 proximate (e.g., abutting) the surface of the leaflet. If desired, multiple cords 60 can be included in the body 18, which can be independently adjustable or have synchronized adjustment, for example, to facilitate control of the diameter of the first expandable member 14 proximate the inferior surface of a leaflet and the diameter of the second expandable member 16 proximate the superior surface of the leaflet.

Returning to FIG. 2, details are provided of the coupler 100. The coupler 100 can comprise a plurality of flexible arms 104 and a plurality of stabilizer members 108. The flexible arms 104 can comprise apertures 112, ports 114, and eyelets 116.

The flexible arms 104 can be configured to pivot between a first or release configuration (FIG. 2) and a second or coupled configuration (FIG. 1). In the first configuration, the flexible arms 104 extend radially outwardly relative to the stabilizer members 108. In the second configuration, the flexible arms 104 extend axially parallel to the stabilizer members 108 and the eyelets 116 radially overlap, as best shown in FIG. 1. The flexible arms 104 can be configured (e.g., shape-set) so as to be biased to the first configuration.

The expandable positioning device 10 can be releasably coupled to the coupler 100 by inserting the stabilizer members 108 of the coupler into the guide openings 48 of the collar 30. The flexible arms 104 of the coupler 100 can then be pivoted radially inwardly from the first configuration to the second configuration such that the projections 46 of the collar 30 extend radially into the apertures 112 of the flexible arms. The flexible arms 104 can be retained in the second configuration by inserting a distal end portion 40b of the shaft 40 through openings 120 of the eyelets 116, which prevents the flexible arms from pivoting radially outwardly from the second configuration to the first configuration, thereby releasably coupling the expandable positioning device 10 to the coupler 100.

The expandable positioning device 10 can be released from the coupler 100 by proximally retracting the shaft 40 relative to the coupler such that the distal end portion 40b of the shaft withdraws from the openings 120 of the eyelets 116. This allows the flexible arms 104 to pivot radially outwardly from the second configuration to the first configuration, which withdraws the projections 46 of the collar 30 from the apertures 112 of the flexible arms 104. The stabilizer members 108 can remain inserted into the guide openings 48 of the expandable positioning device 10 during and after the flexible arms 104 are released. This can, for example, prevent the expandable positioning device 10 from moving (e.g., shifting and/or rocking) while the flexible arms 104 are released. The stabilizer members 108 can then be withdrawn from the guide openings 48 of the expandable positioning device 10 by proximally retracting the coupler 100 relative to the expandable positioning device, thereby releasing the expandable positioning member from the coupler.

With reference to FIG. 1, the shaft 33 of the implant delivery catheter 32 and the expandable positioning device 10 can be introduced into the heart, proximate an implantation site, through an outer catheter 60. Prior to delivering the expandable positioning device 10 to the heart, a guidewire 64 can be positioned at the appropriate implantation location, and the expandable positioning device delivered over the guidewire. For example, a needle or similar device can be used to pierce a heart valve location at a desired implantation site.

As described in further detail with reference to FIGS. 3-9, the expandable positioning device 10, coupled to the implant delivery catheter 32 via the coupling device 100, can be delivered over the guidewire to an implantation site so as to position the first expandable member 14 against an inferior leaflet surface and the second expandable member 16 against the superior leaflet surface. The first and second expandable members 14, 16 can be expanded to a desired degree, with expansion of the first expandable member reorienting the leaflet to provide a desired degree of coaptation improvement, and the second expandable member subsequently being expanded to secure the expandable positioning device 10 at the implantation site.

The shaft 40 and guidewire 64 can then be withdrawn proximally through the expandable positioning device 10, and through the coupling device 100. When the distal end portion 40b of the shaft 40 is withdrawn proximally through the eyelets 116, the coupling device 100 assumes the first (release) configuration, allowing the coupling device, hypotube (shaft 40), guidewire 64, and delivery catheter 60 to be withdrawn from the body, and leaving the expandable positioning device 10 secured at the implantation site.

The first and second expandable members 14, 16 (and, more generally, expandable members and other fluidly connected members of an expandable positioning device 10) can be filled with fluids (gases and/or liquids) and/or other materials (e.g., an expandable mass, such as a hydrogel) that provide a desired degree of biological compatibility and physical properties, including low permeability relative to material from which the expandable positioning device 10, or its components, may be constructed, density, weight, or viscosity. Typically, the material used to fill the expandable members 14, 16 is selected to be biocompatible in case the exterior surface of the expandable members ruptures or otherwise becomes compromised, if any of the material permeates through a material from which the exterior surface of the body 18 is made, or in case the nose cone 26, collar 30, or other component of the expandable positioning device 10 experiences a leak.

If the material from which the expandable members 14, 16 are formed is sufficiently robust, the expandable members can be filled with a gaseous fluid, such as an inert gas (e.g., a gas that will not undergo chemical reactions, or at least undesired chemical reactions, with the body or components of the expandable positioning device 10 under delivery conditions or after implantation). Suitable gases can include nitrogen, carbon dioxide, helium, and argon, including mixtures thereof. Other gases, such as oxygen, may be included in mixtures of gasses, such as air.

In other cases, the fluid can be a liquid, such as a saline solution, or a gel, such as a silicone material, or another solid or semi-solid material, such as a hydrogel. In some implementations, fluids can be introduced into the expandable members 14, 16 in a liquid or gel form, and then allowed to set/solidify, or cure, after the expandable positioning device 10 has been appropriately positioned and expanded to a desired degree. For example, an epoxy material can be delivered to the expandable members 14, 16 in liquid or gel form, and subsequently allowed to harden, or biocompatible photopolymers can be employed. Using a material that subsequently forms a solid (or at least more rigid) material can help provide addition structural integrity to the expandable members, 14, 16, including resisting changes (deformation) due to the contractions of the heart and fluid flow about the expandable positioning device 10. However, the use of gaseous, liquid, or gel fill materials can be beneficial, as it may facilitate later removal of the expandable positioning device 10 (e.g., the fill material can be suctioned from the expandable positioning device and the device removed in the reverse sequence of steps as its implantation) or later adjustment of the degree of expansion of one or more of the expandable members 14, 16 (e.g., removing fluid or adding fluid to an expandable member). In cases where the fill material or inflation medium comprises a solid or semi-solid material, such as a hydrogel, the material can be introduced into the expandable members 14, 16 in the form of small particles, such as beads (e.g., hydrogel beads).

The materials used to fill, or inflate, the expandable members 14, 16 can be the same or different, such as using materials having different states (phases) of matter (e.g., gas, liquid, gel, or solid) in the different expandable members, or using materials having the same state of matter, but different properties or compositions. For example, a less dense material may be used in the first expandable member 14, which may provide buoyancy or otherwise improve the amount of lift provided to the posterior mitral valve leaflet by the first expandable member 14. A denser material can be used in the second expandable member, to push the second expandable member 16 against the superior surface of the posterior mitral valve leaflet.

A practitioner can select a combination of material properties and expansion levels to provide a desired degree of repositioning forces (from the first expandable member 14) and securing forces (from the second expandable member 16). For example, use of a more dense material in the second expandable member 16 may allow less expansion to be used to provide a given securing force, while use of a more buoyant material in the first expandable member 14 may allow less expansion to be used to provide a given repositioning force.

The expandable members 14 and 16 may be in fluid communication in some embodiments, and not in fluid communication in other embodiments. For example, the neck portion 52 can allow fluid communication between the first and second expandable members 14, 16 (e.g., the sealing member 42 can be omitted). In some cases, maintaining fluid communication between the first and second expandable members 14, 16 can allow the first and second expandable members to have a common degree of inflation, and, at least in some examples, shape.

In other cases, the expandable positioning device 10 can be constructed such that pressure will be differentially distributed within the expandable positioning device 10, or that the first and second expandable members 14, 16 otherwise have different shapes or levels of expansion. For example, the first and second expandable members 14, 16 can be constructed from different materials, such that one material is less compliant than the other, in which case the more compliant material will typically experience a greater degree of expansion than the less compliant material. The first and second expandable members 14, 16 can also be provided with different shapes or volumes, which can affect the degree of expansion within each of the expandable members. For example, the first expandable member 14 may have a larger volume (such as provided by a larger size) than the second expandable member, such as to abut the heart wall proximate the inferior surface of the posterior mitral valve leaflet, with an opposite portion of the second expandable member abutting the anterior surface of the posterior mitral valve leaflet, moving the posterior mitral valve leaflet to have improved coaptation with the anterior mitral valve leaflet.

In other cases, the first and second expandable members 14, 16 are not in fluid communication (or fluidly sealed from each other). Having expandable members 14, 16 not in fluid communication can provide benefits, such as allowing different inflation media or other materials to be used in the different expandable members, facilitating expansion of the expandable members to different degrees, or facilitating implantation or removal of an expandable positioning device 10. During implantation, the first and second expandable members 14, 16 can be inflated to differing degrees, if desired. The first and second expandable members 14, 16 can be separated by a seal (for example, the sealing member 42) disposed within the neck portion 52.

After the positioning device 10 is delivered to the target location (e.g., with the first expandable member within a ventricle and the second expandable member 16 is in an atrium on the same side of the heart), the shaft 40 can be retracted from the nose cone 26 until the distal end 40b of the shaft is positioned within the first expandable member 14. The shaft 40 can be used to deliver an inflation medium to the first expandable member 14 until the first expandable member has been inflated to a desired degree. The shaft 40 can then be further retracted proximally until the distal end 40b is located within the second expandable member 16. When the shaft 40 is retracted from the first expandable member 14, the seal (e.g., sealing member 42) separating the first expandable member from the second expandable member 16 can close, causing the inflation medium to be retained within the first expandable member. When the second expandable member 16 has been filled to a desired degree, the shaft 40 can be withdrawn from the expandable positioning device 10.

In at least some cases, the size of the expandable members 14, 16 can be alternatively increased and reduced during an implantation procedure. For example, an inflation medium (e.g., fluid) can be provided to, or removed from, the respective expandable member, multiple times during an implantation procedure. For example, an inflation medium can be added to the first expandable member 14, then added to the second expandable member 16. Based on the expansion of the second expandable member 16, or assessment of the location or function of the expandable positioning device 10, the size of the expanded member can be adjusted, such as by adding inflation medium to, or removing inflation medium from, the first expandable member 14. This process can continue until both expandable members 14, 16 have been inflated to a desired degree.

The expandable members 14, 16, and the expandable positioning device 10 generally, can be shaped or dimensioned so as to provide desired repositioning (in the case of the first expandable member 14) and securing (in the case of the second expandable member 16). The expandable members 14, 16 can be dimensioned to extend over a desired portion of a leaflet (e.g., a particular radial length and circumferential length), or a portion of multiple leaflets. In some cases, the first and second expandable members 14, 16, have the same shape, such as a generally spherical shape that extends away from the neck portion 52. As the first expandable member 14 is constrained by the nose cone 26 and the neck portion 52, and the second expandable member 16 is constrained by the neck portion and the collar 30, the expandable members may have a spheroidal or ellipsoidal shape rather than being completely spherical. In addition, it may be desirable to dimension the expandable members 14, 16 such that they produce a more flattened shape when expanded, such as to increase the surface area in contact between the first or second expandable members 14, 16 and a respective surface of the posterior mitral valve leaflet.

While in some cases expandable members 14, 16 are at least generally symmetric with respect to an axis orthogonal to a horizontal plane that passes through a valve leaflet, in other cases, one or more of the expandable members can be asymmetrical. For example, an expandable member, particularly the first expandable member 14, can have shapes such as a cylindrical shape, C, D, L, U, or horseshoe shapes (which may be disposed under the free edges of the posterior mitral valve leaflet), or a dog bone shape. The shape of the first expandable member 14 can be selected to abut a portion of the mitral valve leaflet (or a leaflet of one of the other native heart valves) to be repositioned superiorly and/or anteriorly, and, at least in some cases, to abut the posterior wall of the left ventricle to provide an opposing force to a force lifting the posterior mitral valve leaflet superiorly and/or anteriorly. An expandable member 14, 16 can be oversized relative to the anatomy at its implantation environment, such that as the expandable member expands, it abuts the surface of a leaflet or the heart wall, which can increase expansion of the expandable member in opposing direction, such as expanding towards the edge of the posterior mitral valve leaflet, causing the posterior mitral valve leaflet to be moved, typically, superiorly and anteriorly.

FIGS. 3-9 illustrate an example method for delivering the expandable positioning device 10 into a patient's heart, expanding the device to provide a desired degree of leaflet repositioning to improve leaflet coaptation and securing the device to a heart valve leaflet. Although FIGS. 3-9 illustrate implantation of the expandable positioning device 10 on the posterior mitral valve leaflet, an analogous procedure can be used to deliver the device to other heart valve leaflets. In addition, although FIGS. 3-9 illustrate an expandable repositioning device 10 that repositions/is secured to a single leaflet, devices that reposition at a least a portion of multiple leaflets/are secured to multiple leaflets can be implanted in an analogous manner. An exemplary delivery apparatus for implanting the device 10 can include the previously mentioned implant delivery catheter 32 (the shaft 33 of which is shown in FIGS. 3-9), a steerable intermediate catheter 60, and an outer catheter 70.

Figure 3:
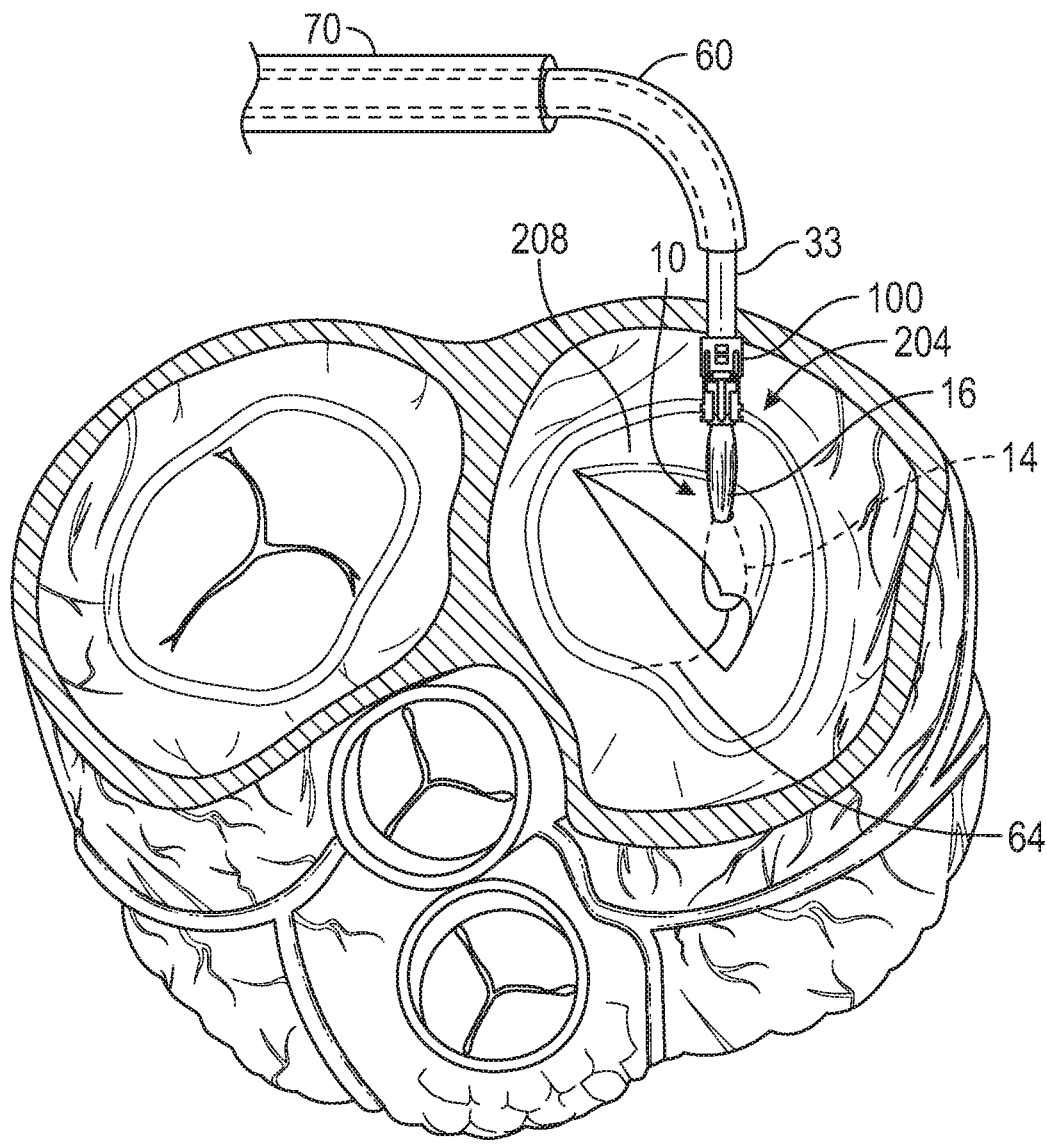
FIGS. 3 and 4 are, respectively, a perspective view of a cross section of a heart, and a cross-sectional view of the left side of the heart, showing the expandable positioning device and delivery device of FIGS. 1 and 2 in an implanted, but unexpanded, state.
Figure 4:
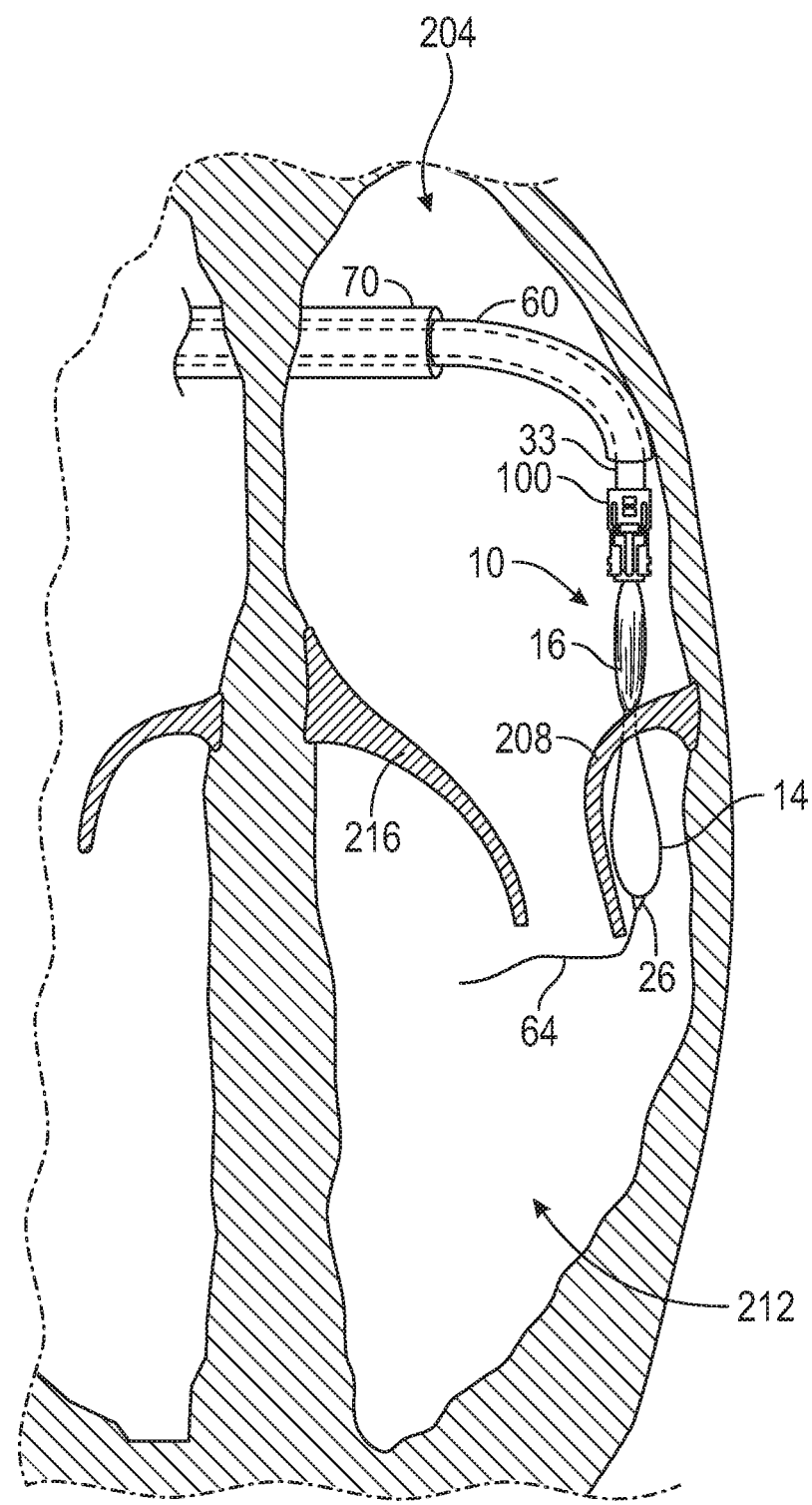

With reference first to FIGS. 3 and 4, using a transcatheter procedure, the delivery apparatus can be advanced into the left atrium 204 over a guidewire 64. For example, the outer catheter 70 can be advanced into the right atrium of the heart via the inferior or superior vena cava and advanced across the interatrial septum until the distal end portion of the outer catheter 70 is located within the left atrium. The outer catheter 70 can have a steering mechanism (e.g., a pull wire and a corresponding adjustment mechanism on a handle of the catheter 70) to steer or adjust the distal end portion of the catheter 70. For example, the curvature of the distal end portion of the catheter 70 can be adjusted such that the distal end portion extends from the septum and curves downwardly toward the mitral valve.

The intermediate catheter 60 can be advanced from the outer catheter 70 within the left atrium. The intermediate catheter 60 also can have a steering mechanism that allows the distal end portion of the catheter 60 to extend downwardly toward the mitral valve. The implant delivery catheter 32 can be advanced from the intermediate catheter 60 for implantation. As best shown in FIG. 4, the curvatures of the outer catheter 70 and the intermediate catheter 60 are such that the implant catheter 32 and the positioning device 10 generally extend perpendicularly to a plane defined by the native mitral valve annulus. As the delivery apparatus is inserted into the patient's body and advanced into the heart, the expandable positioning device 10 can be retained within the distal end portion of the intermediate catheter 60, which serves as a sheath for the positioning device 10. The positioning device 10 can be advanced from the intermediate catheter 60 after the intermediate catheter is extended into the left atrium as shown in FIG. 4.

Further details of the delivery apparatus are disclosed in co-pending application Ser. No. 15/973,892, filed May 8, 2018, which is incorporated herein by reference. Any of the features or components of the delivery apparatus disclosed in application Ser. No. 15/973,892 can be incorporated into the delivery apparatus used for implanting the expandable positioning device 10. Further details regarding the construction of a steerable catheter are disclosed in U.S. Patent Publication No. 2016/0158497, which is incorporated herein by reference. The intermediate catheter 60 and the other catheter 70 can have steering mechanisms as disclosed in U.S. Patent Publication No. 2016/0158497.

A needle (not shown) can be used to puncture the posterior mitral valve leaflet 208. In some cases, for example, a separate needle can be advanced over the guidewire 64, pushed through the target leaflet (the posterior leaflet in the illustrated example), and then removed from the body. In other cases, the needle can be positioned at the distal end of the guidewire 64 and pushed through the leaflet using the guidewire, or alternatively, the guidewire itself can be used to penetrate the leaflet. After the guidewire 64 is inserted through the leaflet, the positioning device 10 is advanced over the guidewire with the nose cone 26 facilitating crossing of the leaflet. In other embodiments, the distal end of the nose cone 26 can be adapted to penetrate the leaflet.

The expandable positioning device 10 can be advanced until the first expandable member 14 is positioned underneath the posterior mitral valve leaflet 208, in the left ventricle 212 (FIG. 4), and the second expandable member 16 is positioned above the posterior mitral valve leaflet in the left atrium 204

Figure 5:
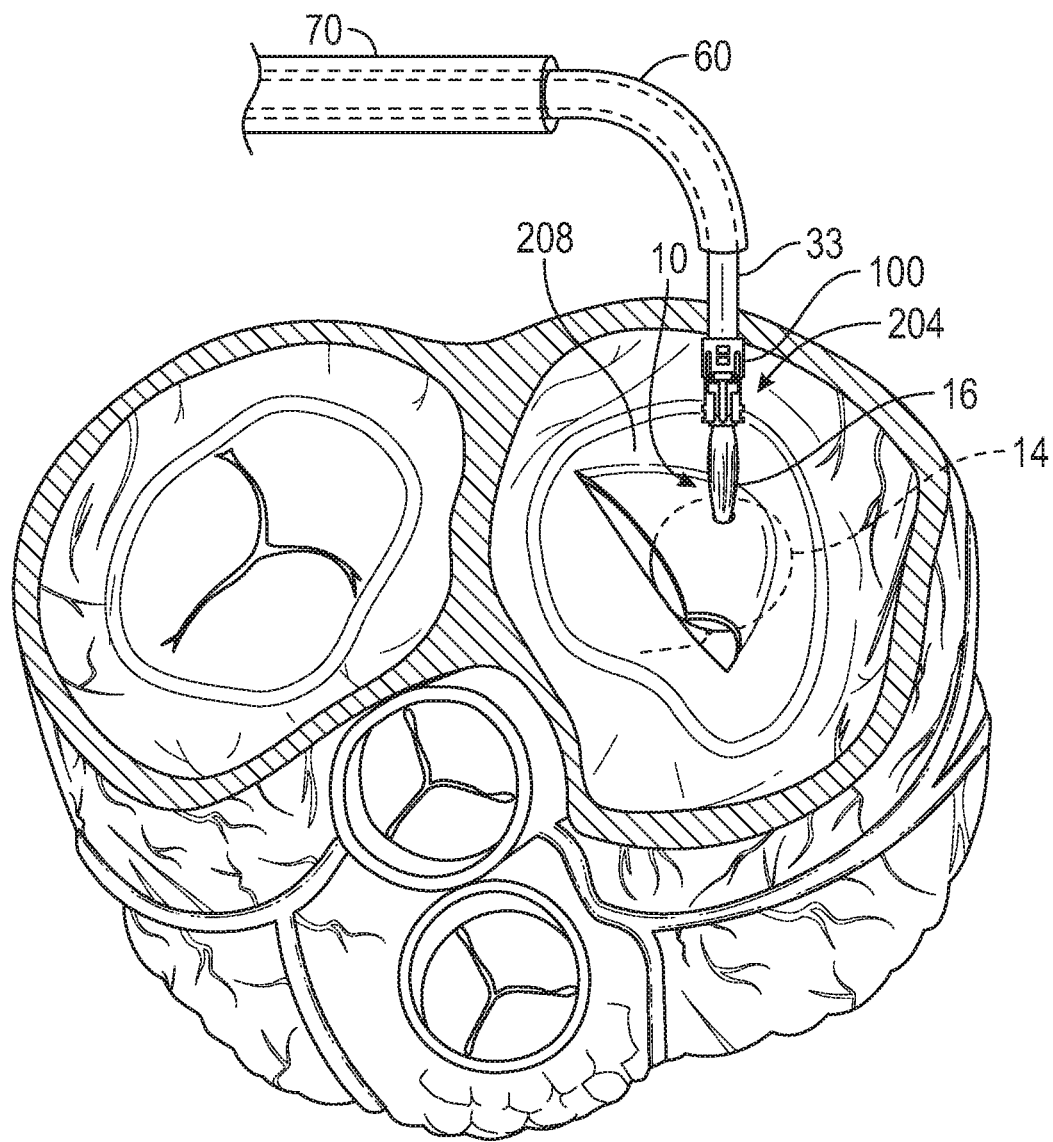
FIGS. 5 and 6 are, respectively, a perspective view of a cross section of a heart, and a cross-sectional view of the left side of the heart, showing the expandable positioning device and delivery device of FIGS. 1 and 2 in an implanted, partially-expanded state, where a ventricular expandable member is expanded and an atrial expandable member is unexpanded.
Figure 6:
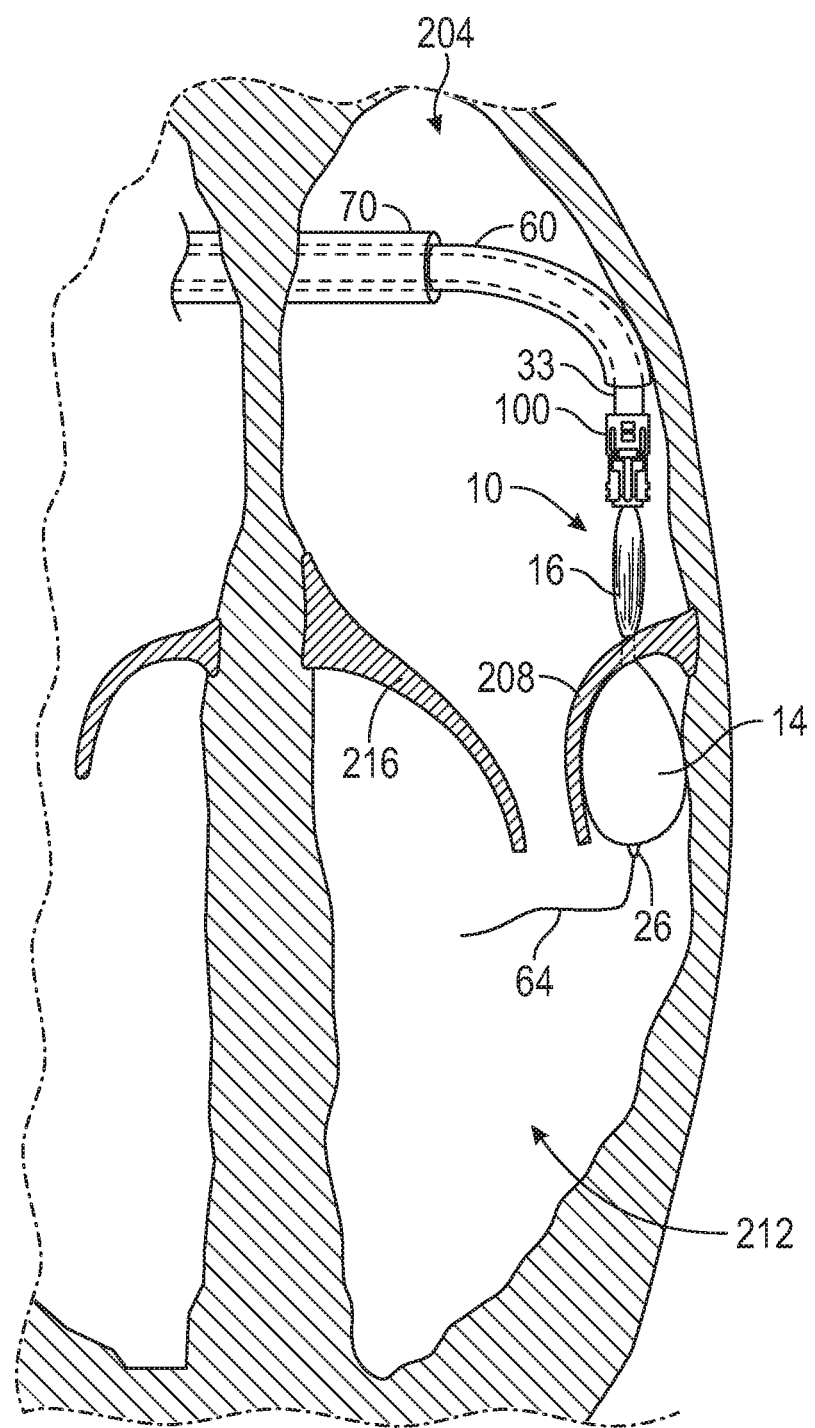

With reference to FIGS. 5 and 6, the first expandable member 14 can be inflated such that it causes the posterior mitral valve leaflet 208 to move anteriorly and/or superiorly, providing improved coaptation with the anterior mitral valve leaflet 216. When the expandable positioning device 10 includes a radiogenic or echogenic marker, the marker can be used to confirm delivery and the correct position of the expandable positioning device within the heart. If desired, the expandable positioning device 10 can include additional radiogenic or echogenic markers, such as at the circumferential edges of the first expandable member 14, to assess the degree of expansion of the first expandable member, as well as its relative position within the heart. Functional imaging studies can be used to assess the flow of blood through the mitral valve, with the first expandable member 14 being expanded or contracted until regurgitation is minimized.

Figure 7:
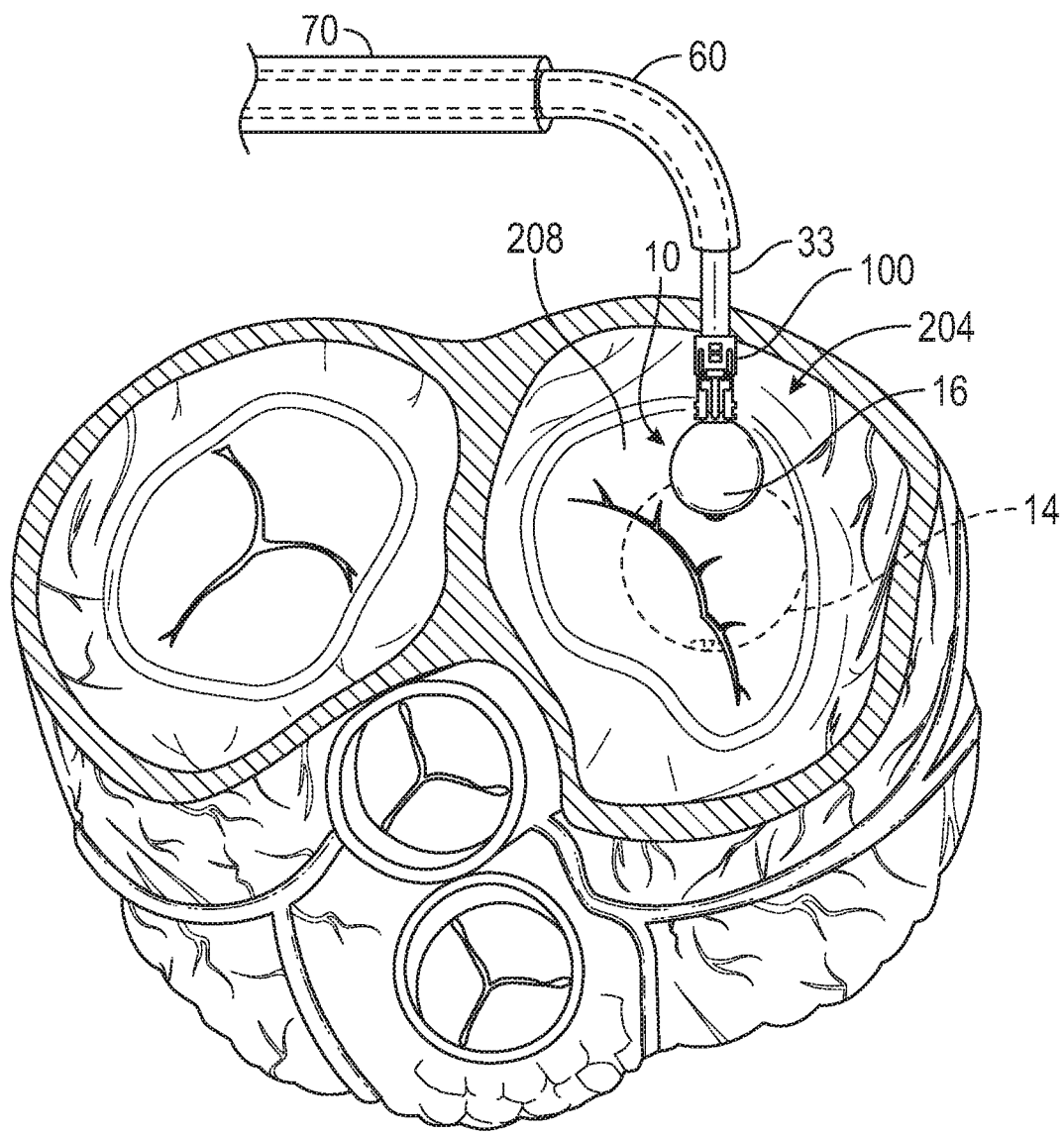
FIGS. 7 and 8 are, respectively, a perspective view of a cross section of a heart, and a cross-sectional view of the left side of the heart, showing the expandable positioning device and delivery device of FIGS. 1 and 2 in an implanted, fully-expanded state, where ventricular and atrial expandable members are expanded.

With reference to FIGS. 7 and 8, when the first expandable member 14 has been placed at a desired position, and inflated to a desired degree, the second expandable member 16 can be inflated to secure the expandable positioning device 10 to the posterior mitral valve leaflet 208. That is, inflation of the first expandable member 14 and the second expandable member 16 causes the expandable members to expand towards each other, compressing the posterior mitral valve leaflet 208 between them, and thus securing the expandable positioning device 10 to the leaflet.

FIGS. 7 and 8 illustrate the expandable positioning device 10 implanted on the posterior mitral valve leaflet 208, with the first expandable member 14 and the second expandable member 16 inflated to their final expansion points or sizes. That is, the first expandable member 14 is inflated to provide a desired degree of repositioning of the posterior mitral valve leaflet 208, and the second expandable member 16 is inflated to provide a desired degree of securing force. The expandable positioning device 10 can be maintained at the implantation site, and at a desired orientation, both through the compressive forces exerted by the expandable members 14, 16 on the leaflet 208, as well as by the expandable members having a diameter larger than an opening in the leaflet through which the first expandable member 14 was inserted.

With reference to FIGS. 8 and 9, the positioned device 10 can be configured such that the nose cone 26 recedes into the first expandable member 14 when it is expanded to minimize contact with the flow of fluid within the left ventricle 212. In addition, as shown in FIG. 9, the rigid ring 54 can be enveloped by the expanded first and second expandable members 14, 16. Advantageously, the second expandable member 16 distributes pullout forces across a relatively larger surface area of the leaflet if pullout forces increase due to remodeling of the native annulus and/or the leaflet 208 and/or pressure changes. When expanded, the second expandable member 16 desirably has a relatively low profile to avoid contact with the wall of the left atrium.

As described above, and with reference to FIG. 9, in some cases, an expandable positioning device 10 can include one or more cords 60 that can be used to adjust one or more dimensions of the expandable positioning device, such as a diameter of the first expandable member 14 or the second expandable member 16. In FIG. 9 the cord 60 is shown as encircling the ventricular, first expandable member 14. Thus, pulling the cord 60 proximally can reduce the diameter of the cord.

The cord 60 can be connected to the first expandable member 14 such that the cord is moveable relative to the first expandable member, and the expansion or reduction of the diameter of the cord causes a corresponding expansion or reduction of the diameter of the first expandable member. In a specific example, the cord 60 can extend about the interior surface of the first expandable member 14, such as passing through a sleeve, or a series of retaining loops 222 fixed to the interior surface of the first expandable member. In alternative embodiments, the cord 60 and the retaining loops 222 can be positioned on the exterior of the expandable member 14.

The diameter of the cord 60 can be controlled, in a particular implementation, using a tether 224, such as a length of suture, looped around a portion of the cord. As the tether 224 is pulled proximally (in the direction of arrow 230), such out of the collar 30, tension is applied to the cord 60, causing the cord to be drawn proximally towards, and in some cases through, the collar. Once the cord 60 has been adjusted to have a desired diameter, the tether 224 (and/or cord) can be secured using a suitable securement or locking device 228, such as a suture clip. The locking device 228 can place the tether 224 and/or cord 60 under tension, maintaining the selected diameter of the cord.

The locking member 228 can be a suture clip, or another type of fastener that can be deployed from a catheter and secured to a suture within the patient's body. Various suture clips and deployment techniques for suture clips that can be used in the methods disclosed in the present application are disclosed in U.S. Publication Nos. 2014/0031864 and 2008/0281356 and U.S. Pat. No. 7,628,797, which are incorporated herein by reference.

Figure 10:
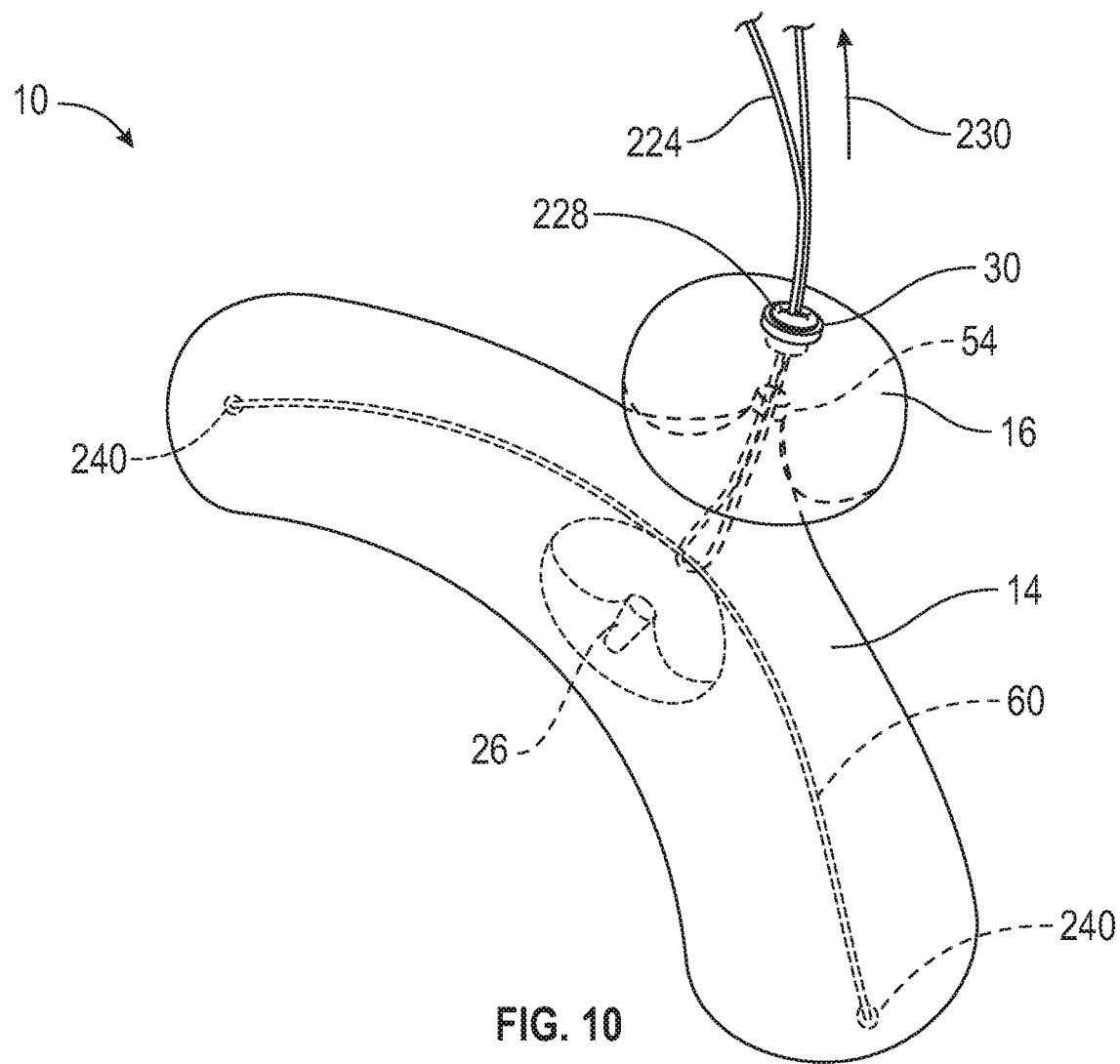
FIG. 10 is a perspective view of another implementation of the expandable positioning device of FIGS. 1 and 2, in a fully expanded state, such as after implantation and expansion as shown in FIGS. 7 and 8, with a cord useable to adjust the separation of arms of a C-shaped expandable member positioned below a leaflet surface.

FIG. 10 illustrates an alternative embodiment of an expandable positioning device 10 that includes a cord 60. The cord 60 is shown as coupled to opposing interior portions 240 of the first expandable member 14. The first expandable member 14 is shown as having a generally C-shape, which can correspond to the shape of the posterior mitral valve leaflet 208 between the posterior and anterior commissures (e.g., as shown in FIG. 8).

The geometry and construction (e.g., stiffness) of the first expandable member 14 can be selected such that, as the first expandable member is expanded, the first expandable member expands in the commissure-commissure direction (e.g., parallel to the free edges of the leaflet 208 and the valve opening). Additional expansion causes the diameter (e.g., perpendicular direction to the free edges of the leaflet 208, as shown in FIG. 8) to increase, causing the leaflet to move anteriorly and superiorly to improve coaptation with the anterior leaflet 216. The commissure-commissure expansion can be controlled using the cord 60. Similarly to FIG. 9, pulling the cord 60 proximally (in the direction of arrow 230) using the tether 224, such as out of the collar 30, causes the cord to be drawn proximally toward, and in some cases through, the collar. Once the cord 60 has been adjusted to have a diameter (and a corresponding commissure-commissure expansion of the first expandable member 14, or distance between the ends of the C-shaped first expandable member 14), the tether 224 (and/or cord) can be secured using a suitable locking device 228, such as a suture clip. The locking device 228 can place the suture and/or cord 60 under tension, maintaining the selected diameter of the cord.

Figure 11:
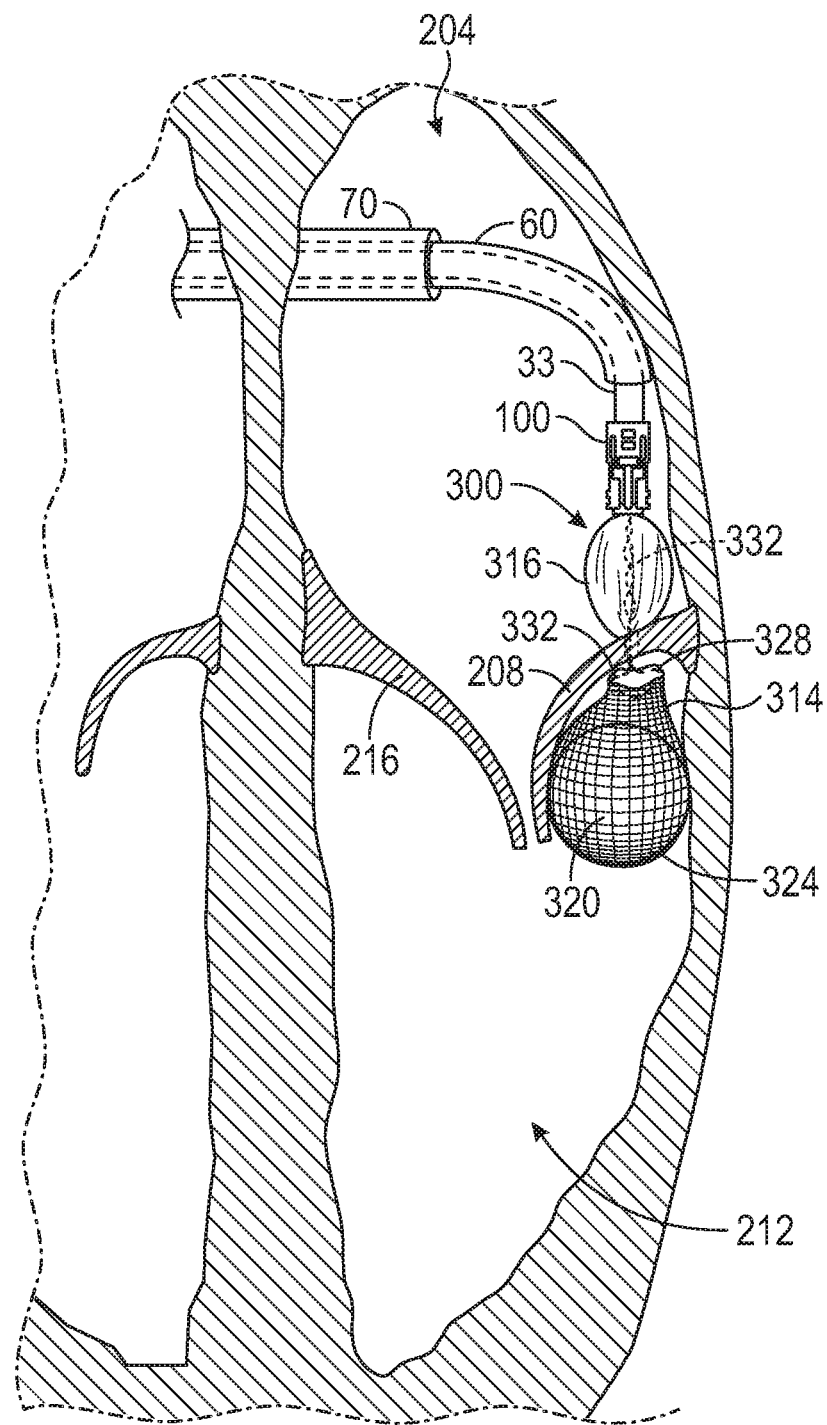
FIG. 11 is a cross-sectional view of the left side of the heart, showing an expandable positioning and delivery device implanted in the heart and in a fully expanded state, where the expandable positioning device includes a mass of an expandable material, such as a swellable material.

FIG. 11 illustrates an expandable positioning device 300 implanted on the posterior mitral valve leaflet 208, according to another embodiment. The expandable positioning device 300 can include a first expandable member 314 and a second expandable member 316. The first expandable member 314 can include a mass 320 of an expandable material, such as a swellable material, prior to introduction into the patient's body. The first expandable member 314 can comprise an enclosure 324, such as in the form of a sack or envelope, that contains the mass 320. The enclosure 324 may have a variable-width or variable-diameter opening 328. A cord 332 can be coupled to the enclosure 324, about the opening 328. As the cord 332 is placed under tension, the width of the opening 328 is reduced, in a similar manner as a purse string or drawstring.

The mass 320 can comprise any suitable expandable material. In some cases, the material can be a polymeric material, such as a hydrogel. Suitable hydrogel materials can include crosslinked carboxymethylated chitosan/poly(ethylene glycol) polymers, lignin hydrogels, and poly (N-isopropylacrylamide) hydrogels. Suitable hydrogels are typically biocompatible and physiologically inert.

The mass 320 can be selectively expandable. In some cases, the mass 320 is expandable after the expandable positioning device 300 is introduced into the heart. For example, the mass 320 may be brought in contact with suitable fluids to cause expansion of the first expandable member 314, such as blood. When contacted with physiological fluids, the amount of material in the mass 320, as well as its expansive properties, are typically selected such that the mass 320 will expand to a desired degree after implantation. That is, the amount of material in the mass 320, its size, and maximum expansion, can be determined prior to expansion, and exposure to physiological fluids can cause expansion to such predetermined size.

Fluids used to expand the mass 320 can include externally-introduced fluids, such as fluids introduced through the delivery catheter 32. In implementations where the second expandable member 316 comprises an inflatable member, the same fluid used to expand the mass 320 can be used to inflate the second expandable member 316. The mass 320 can include a temperature or pH sensitive material, such as a hydrogel, that expands, and in some cases, contracts, when brought into contact with a fluid having a suitable temperature or pH. The degree of expansion or contraction of the mass 320 can be controlled by the amount of fluid placed in contact with the mass, the amount of time the fluid is kept in contact with the mass, or the temperature or pH or the mass (e.g., a higher temperature or pH fluid may cause a more rapid expansion than a comparatively lower temperature or pH fluid), or combinations of these factors. The mass 320 may also be expanded, and in some cases, contracted, using other stimuli, such electrical stimuli or radiation (e.g., particular wavelengths of light). Again, the degree (e.g., voltage or current, radiation intensity), duration of exposure, or extent of stimulation can affect how rapidly expansion or contraction of the mass 320 occurs, as well as the degree of expansion or contraction. In some cases, the mass 320 can include materials that are responsive to multiple types of stimulation, including having one type of stimulation used to expand the mass and another type of stimulation used to contract the mass.

As discussed, in at least some cases, the mass 320 can be both expanded and contracted. Having a mass 320 that can be expanded, and then contracted, can provide a number of benefits. For example, during implantation, a physician can expand the mass 320, gauge the effect of the expandable positioning device 300 on heart function (e.g., a reduction in valve regurgitation), and expand or contract the mass 320 as desired to try and improve heart function. In addition, having a contractable mass 320 can be beneficial if the expandable positioning device 300 is to be removed from the heart.

The mass 320 can be prepared in a desired shape, such as to conform to native anatomy and provide a desired degree of leaflet repositioning. The mass 320 may also be compliant. Having a compliant mass 320 can facilitate conforming the first expandable member 314 to native anatomy, as well helping the device 300 adapt to anatomical changes that may occur after implantation of the expandable positioning device 300. For example, if a higher degree of pressure is placed on the mass 320, the mass may respond by contracting. Correspondingly, if pressure on the mass 320 is reduced, the mass may expand.

The mass 320 can be formed from a unitary mass of material, such as hydrogel, or can be composed of multiple, discrete particles of the same or varying sizes, such as multiple hydrogel beads. In some cases, when the mass 320 is formed from multiple particles, the particles need not be joined together. For example, the mass 320 can include multiple hydrogel beads, which can move with respect to one another inside the enclosure 324, but are otherwise contained within the enclosure so as to function similarly to a unitary mass. In other cases, when the mass 320 is formed from multiple particles, the particles can be adhered or otherwise joined together. In some embodiments, the mass 320 is included in the enclosure 324 prior to the device 300 being inserted into a patient. In other cases, all or a portion of the mass 320 can be introduced into the enclosure 324 during an implantation procedure, such as after the device 300 has been inserted through a leaflet.

The enclosure 324 can be fluid-impermeable, in some embodiments, such as when the mass 320 is to be expanded other than through contact with a fluid, or when an amount of fluid is to be retained within the enclosure 324, and thus also contribute to expansion of the first expandable member 314. Any of the materials described above for forming the expandable members 14, 16 can be used to form the enclosure 324.

In other cases, the enclosure can be permeable, for example, having a mesh structure (e.g., a braided or woven construction). Having a permeable enclosure 324 can be beneficial when physiological fluids, such as blood, are to be used to expand the mass 320, or when external fluids are used to expand the mass, but such fluids are not desired to be retained within the enclosure. The enclosure 324 can be, for example, any biocompatible fabric or another type of biocompatible textile with a desired degree of porosity to a selected fluid. In particular embodiments, the enclosure 324 can be formed from a polyethylene terephthalate (PET) fabric. In alternative embodiments, the enclosure 324 can be formed from a non-textile sheet or membrane formed from any of the materials described above for forming the expandable members 14, 16, but are also formed with apertures or perforations (e.g., formed by laser cutting) with apertures or perforations sized to allow a desired degree of porosity to a selected fluid.

If the mass 320 is to be expanded by contact with blood in the heart, the enclosure can be selected to have openings large enough that allow blood in the heart to come into contact with the mass 320 inside the enclosure but small enough to contain the mass 320 or particles that form the mass 320 inside the enclosure. When formed from a woven fabric or a braided material, the weave or braid density can be selected to have openings that perform this particular function.

The enclosure 324 can be expandable to accommodate expansion of the mass 320. In other cases, the enclosure 324 can have an at least substantially fixed interior volume. The enclosure 324 can be constructed with other properties, such as being constructed from a material that encourages tissue ingrowth, such as a PET fabric. The cord 332 can be coupled to the enclosure 324 by any suitable means, such as being secured within a channel or sleeve formed in the enclosure around the opening 328, or retained by passing through a plurality of loops coupled to or formed in the enclosure. Or, the cord 332 can be threaded through or woven into the material of the enclosure 324.

As shown in FIG. 11, the cord 332 can pass through the leaflet 208, and into the interior of the second expandable member 316. In turn, the cord 332 can extend through the coupling member 100 and optionally into the implant delivery catheter 32 (the shaft 33 of which is shown in FIG. 11). The cord 332 can be in the form of an elongated loop, as shown in FIG. 11, which can extend proximally from the enclosure 324 through the second expandable member 316, proximally through the delivery catheter 32, and can have free ends located at or in the vicinity of the proximal end of the delivery apparatus. The free ends of the cord 332 can be exposed at the proximal end of the delivery apparatus so that a user can grasp the ends and manually apply force directly to the cord to increase the tension in the cord and reduce the size of the opening 328. Alternatively, the free ends of the cord 332 can be operatively connected to one or more actuators (e.g., one or more knobs or levers) on a handle of the delivery apparatus, which, when actuated, can increase and decrease the tension in the cord to vary the size of the opening 328.

In another embodiment, the cord 332 can form a loop around the opening 328 and one end (the distal end) of the cord 332 can be secured to the enclosure, such as by adhering or fastening (e.g., tying a knot) the cord end to material of the enclosure 324, or to a mounting structure coupled to, or formed on, the enclosure. The cord 332 can then extend proximally through the second expandable member 316 and through the delivery catheter 32, and the opposite end (proximal end) of the cord can be exposed at the proximal end of the delivery apparatus for manipulation by a user or can be operatively coupled to an actuator (e.g., a knob or lever) on a handle of the delivery apparatus, which actuator is configured to increase and decrease tension in the cord to vary the size of the opening 328.

The expandable positioning device 300 can have a connecting member (e.g., similar to the neck portion 52 of FIG. 1) disposed between and interconnecting the first expandable member 314 and the second expandable member 316. The positioning device 300 can further include a cord locking member, such as a suture clip, located at a convenient location on the positioning device 300 to maintain tension on the cord 332 after being appropriately tensioned. For example, the cord locking member can be located on or within the connecting member or at the proximal end of the second expandable member 316. After being appropriately tensioned and the cord locking member is activated to maintain tension in the cord, the portion of the cord proximal to the cord locking member can be severed and removed from the patient. In other embodiments, a cord locking member, such as a suture clip, can be deployed from the delivery catheter and advanced distally along cord 332 after the positioning device 300 is implanted on the native leaflet. After positioning the cord locking member at the implanted positioning device, the portion of the cord proximal to the cord locking member can be severed and removed from the patient.

The cord 332 can be used to cinch the opening 328 to a desired diameter, which can help retain the mass 320 within the enclosure 324. Having a variable-width opening 328 can, among other benefits, allow the enclosure 324 to better adapt to expansion and contraction of the mass 320, such as relieving strain the might be caused by expansion of the mass.

In some embodiments, the second expandable member 316 can be the second expandable member 16 of the device 10, such as being a balloon or similarly inflatable component. In further embodiments, the second expandable member 316 can be constructed in a similar manner as described for the first expandable member 314. An expandable material used in the second expandable member 316 can be the same as, or different than, the expandable material used for the expandable mass 320. In yet further embodiments, the device 300 can omit a second expandable member 316, and can be secured to a leaflet in another manner, such as by using hooks or barbs, or using an anchor (e.g., a T-bar) disposed on the superior surface of the leaflet or embedded in heart tissue (e.g., the wall of the left ventricle). In yet further embodiments, a positioning device can include an expandable material in a second expandable member, disposed against a superior leaflet surface, using an expandable material to help anchor the device, and can include a first expandable member (e.g., a balloon) that is disposed against an inferior leaflet surface and is inflated to provide a desired degree of leaflet repositioning, as described for the expandable member 14 of the positioning device 10.

The positioning device 300 can be delivered and implanted using the delivery apparatus and techniques described above for the positioning device 10 and shown in FIGS. 3-8, except that instead of introducing an inflation medium into the second expandable member 318, the mass 320 is expanded as described above to expand the second expandable member 318.

Various changes may be made to the expandable positioning device 300. For example, the first expandable member 314 can have an enclosure 324 that does not include an opening 328 (e.g., the first expandable member has an integral or contiguous surface), in which case the cord 332 can be omitted. Or, rather than passing into second expandable member 316, the cord 332 can be secured externally to the expandable positioning device 300.

The expandable positioning devices 10, 300 can provide a number of advantages. For example, a particular expandable member 14, 16, 314, 316 can be expanded to provide a desired amount of repositioning or securing force. Thus, the expandable positioning devices 10, 300 can be standardized components that can be expanded to differing degrees to account for the size of a particular patient's heart, as well as the relative positions of the posterior and anterior mitral valve leaflets, and the degree of repositioning needed to improve leaflet coaptation. In addition, the expandable members 14, 16, 314, 316 can be made from (and filled with) a compliant material, which allows the expandable members to conform to specific patient anatomies.

The expandable positioning devices 10, 300 also facilitate implantation, as the delivery method does not require a catheter, or other portion of the delivery device 32, to extend between the coaptation edges of the leaflets of the mitral valve, which allows for real time assessment of mitral valve regurgitation during implantation. This assessment can allow the expansion of the first expandable members 14, 314 to be adjusted to minimize mitral valve regurgitation.

The expandable positioning devices 10, 300 can also provide for enhanced patient safety. In the event a problem is encountered during implantation, or the expandable positioning devices 10, 300 do not provide reduce mitral valve regurgitation to a desired degree, the expandable members 14, 16, 314, 316 can be contracted, and the expandable positioning device removed from the patient. The procedure can also be safer for the patient, as a delivery procedure can avoid catheter manipulation in the ventricle. The expandable positioning devices 10, 300 do not, at least typically, extend into the orifice of the mitral valve (between the native leaflets), thus maintaining a larger effective orifice area, and helping maximize flow through the mitral valve.

The repair devices described herein (e.g., expandable repositioning devices 10, 300) have been described in the context of repairing a native mitral valve leaflet. However, it should be understood that the repair devices can be used to repair leaflets of the other native heart valves, or artificial heart valves or artificial heart valve components (e.g., artificial leaflets), including using various transcatheter techniques (e.g., transatrial, transventricular, etc.). The expandable positioning devices 10, 300 can, for example, be used to reduce or improve valvular regurgitation by improving coaptation between heart valve leaflets. In the case of artificial heart valve leaflets, after implantation of such leaflets, over time, the leaflet may exhibit changed mechanical or structural properties (e.g., sagging), or the shape of the heart or its components may change, such that the heart valve leaflets (e.g., an artificial leaflet and one or more natural leaflets, or multiple artificial leaflets, optionally with a natural leaflet) may no longer coapt to a desired degree. A disclosed expandable repositioning device 10, 300 can be implanted to reposition an artificial leaflet to improve coaptation with one or more other leaflets.

While the expandable repositioning devices 10, 300 have been described as including an expandable atrial member that secures the device to a leaflet, in other embodiments a repair device can include an expandable ventricular member than functions as described above, but the repair device can be secured to the leaflet in another manner. For example, an anchor, such as a t-shaped bar, can be placed proximate the superior leaflet surface and be coupled to the ventricular expandable member. Or, the ventricular expandable member can include barbs or other securing means to attach to the inferior leaflet surface, or the ventricular expandable member can be secured in another manner.

Although a trans-septal delivery technique is described in detail above, any of various other delivery techniques can be used to deliver an expandable positioning device 10, 300 through a patient's vasculature. In a transfemoral procedure, the delivery apparatus can be inserted through a femoral artery and the aorta to the heart in a retrograde direction. Alternatively, the delivery apparatus can be inserted through a femoral vein and the vena cava to the right side of the heart in an antegrade direction, such as for implanting an expandable positioning device 10, 300 on one of the leaflets of the tricuspid valve. In a transventricular procedure, the delivery apparatus can be inserted through a surgical incision made in the chest and at a location on the left or right ventricle to access valves on the left and right sides of the heart. For example, the delivery apparatus can be inserted through an incision made on the bare spot on the lower anterior ventricle wall to access the left ventricle. Similarly, the delivery apparatus can be inserted through a surgical incision on the wall of the right ventricle to access the pulmonary or tricuspid valves. In a transatrial procedure, the delivery apparatus can be inserted through a surgical incision made in the wall of the left or right atrium to access the native valves on the left or right sides, respectively, of the heart. In a transaortic procedure, the delivery apparatus can be inserted through a surgical incision made in the ascending aorta and advanced toward the heart. Further details of delivery techniques for accessing the native valves of the heart are disclosed in U.S. Patent Publication No. 2014/0067052, which is incorporated herein by reference.

It should be noted that the positioning of the disclosed devices (e.g., expandable positioning devices 10, 300) can be confirmed visually using imaging modalities such as fluoroscopy, X-ray, CT, and MR imaging. Echocardiography in either 2D or 3D can also be used to help guide the positioning of the device.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present, or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The present disclosure is not restricted to the details of any foregoing embodiments. The present disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

What is claimed is:

1. A method for improving coaptation of heart valve leaflets, the method comprising:
   inserting a guidewire through a first heart valve leaflet of a heart;
   advancing an expandable positioning device over the guidewire such that a first expandable member of the expandable positioning device is disposed entirely under an inferior surface of the first leaflet and a second expandable member of the expandable positioning device is disposed against a superior surface of the first leaflet;
   expanding the first expandable member such that the first expandable member contacts cardiac wall tissue and the inferior surface of the first leaflet to push the first leaflet toward a second heart valve leaflet of the heart such that coaptation is improved between the first leaflet and the second leaflet;
   expanding the second expandable member to secure the expandable positioning device to the first leaflet, wherein an interior volume of the first expandable member is fluidly sealed from an interior volume of the second expandable member after the expandable positioning device is secured to the first leaflet; and
   removing the guidewire from the heart, wherein the expandable positioning device is left secured to the first leaflet after the guidewire is removed from the heart.

2. The method of claim 1, wherein the first and second expandable members are separated by a neck portion of the positioning device that is positioned within an opening in the first leaflet.

3. The method of claim 2, wherein a sealing member is disposed in the neck portion and fluidly seals the first expandable member from the second expandable member after the act of the expanding the first expandable member.

4. The method of claim 1, wherein at least one of first and second expandable members is filled with a liquid or gel that solidifies after expansion.

5. The method of claim 1, further comprising:
   retracting a shaft through a sealing member at a proximal end of the expandable positioning device; and
   retracting the shaft through a coupling member of a delivery device, thereby releasing the coupling member from a coupled configuration to a decoupled configuration where the expandable positioning device is released from the delivery device.

6. The method of claim 1, further comprising:
   after expanding the first expandable member, retracting a shaft proximally through a seal disposed between the first and second expandable members.

7. The method of claim 6, further comprising:
   after expanding the second expandable member, retracting the shaft through a sealing member at a proximal end of the expandable positioning device; and
   retracting the shaft through a coupling member of a delivery device, thereby releasing the coupling member from a coupled configuration to a decoupled configuration where the expandable positioning device is released from the delivery device.

8. The method of claim 1, wherein the first expandable member comprises a mass of an expandable material.

9. The method of claim 1, further comprising:
   inserting a tube into at least one of the interior volume of the first expandable member or the interior volume of the second expandable member, wherein, for a respective interior volume of an expandable member into which the tube is inserted, expanding the respective expandable member comprises introducing a fluid through the tube; and removing the tube from the expandable positioning device.

10. The method of claim 9, further comprising:
retracting the tube through a sealing member at a proximal end of the expandable positioning device; and
retracting the tube through a coupling member of a delivery device, thereby releasing the coupling member from a coupled configuration to a decoupled configuration where the expandable positioning device is released from the delivery device.

11. The method of claim 9, further comprising:
after expanding the first expandable member, retracting the tube proximally through a seal disposed between the first expandable member and the second expandable member.

12. The method of claim 11, further comprising:
after expanding the second expandable member, retracting the tube through a sealing member at a proximal end of the expandable positioning device; and
retracting the tube through a coupling member of a delivery device, thereby releasing the coupling member from a coupled configuration to a decoupled configuration where the expandable positioning device is released from the delivery device.

13. The method of claim 9, wherein expanding the second expandable member comprises introducing a fluid into the interior volume of the second expandable member through the tube.

14. The method of claim 9, further comprising:
after expanding the first expandable member, retracting the tube into the second expandable member, wherein expanding the second expandable member comprises introducing fluid through the tube into the interior volume of the second expandable member.

15. The method of claim 14, wherein retracting the tube into the second expandable member comprises retracting the tube through a seal disposed between the first expandable member and the second expandable member.

16. The method of claim 9, wherein the removing the tube from the expandable positioning device is carried out after the expanding the first expandable member and the expanding the second expandable member.

17. The method of claim 9, wherein inserting a tube into at least one of the interior volume of the first expandable member or the interior volume of the second expandable member comprises inserting the tube into the interior volume of the second expandable member, the method further comprising:
after expanding the second expandable member, retracting the tube into the first expandable member, wherein expanding the first expandable member comprises introducing fluid through the tube into the second expandable member.

18. The method of claim 9, wherein inserting a tube into at least one of the interior volume of the first expandable member or the interior volume of the second expandable member comprises inserting the tube into the interior volume of the first expandable member, the method further comprising:
after expanding the first expandable member, retracting the tube into the second expandable member, wherein expanding the second expandable member comprises introducing fluid through the tube into the second expandable member.

19. The method of claim 18, wherein retracting the tube into the second expandable member comprises retracting the tube through a seal disposed between the first expandable member and the second expandable member.

20. The method of claim 9, further comprising retracting the tube proximally through a nosecone into an interior volume of the expandable positioning device, the interior volume of the expandable positioning device comprising the interior volume of the first expandable member and the interior volume of the second expandable member, prior to the inserting a tube into at least one of the interior volume of the first expandable member or the interior volume of the second expandable member.

* * * * *